(12) United States Patent
Doherty

(10) Patent No.: US 11,135,175 B2
(45) Date of Patent: Oct. 5, 2021

(54) ACTIVE COMPONENT ENCAPSULATED, PROTECTED AND STABILIZED WITHIN A PROTEIN SHELL

(71) Applicant: ANABIO TECHNOLOGIES LIMITED, Dublin (IE)

(72) Inventor: Sinead Doherty, Dublin (IE)

(73) Assignee: Anabio Technologies Limited, Dublin (IE)

( * ) Notice: Subject to any disclaimer, the term of this patent is extended or adjusted under 35 U.S.C. 154(b) by 45 days.

(21) Appl. No.: 16/504,467

(22) Filed: Jul. 8, 2019

(65) Prior Publication Data

US 2019/0328676 A1 Oct. 31, 2019

Related U.S. Application Data

(62) Division of application No. 14/897,901, filed as application No. PCT/EP2014/062154 on Jun. 11, 2014, now Pat. No. 10,449,157.

(30) Foreign Application Priority Data

Jun. 12, 2013 (EP) .................................... 13171757

(51) Int. Cl.
| | |
|---|---|
| *A61K 38/00* | (2006.01) |
| *A61K 9/50* | (2006.01) |
| *A61K 31/198* | (2006.01) |
| *A23P 10/30* | (2016.01) |
| *A61K 36/67* | (2006.01) |
| *A23L 33/105* | (2016.01) |
| *A23L 33/10* | (2016.01) |
| *A23L 33/175* | (2016.01) |

(52) U.S. Cl.
CPC ............ *A61K 9/5052* (2013.01); *A23L 33/10* (2016.08); *A23L 33/105* (2016.08); *A23L 33/175* (2016.08); *A23P 10/30* (2016.08); *A61K 9/5089* (2013.01); *A61K 31/198* (2013.01); *A61K 36/67* (2013.01)

(58) Field of Classification Search
None
See application file for complete search history.

(56) References Cited

U.S. PATENT DOCUMENTS

2003/0215506 A1 11/2003 Kuhrts
2007/0065511 A1* 3/2007 Tallon .................. A61K 9/2068
424/468

FOREIGN PATENT DOCUMENTS

| WO | WO2007/069078 | 6/2007 |
| WO | WO2008/017962 | 2/2008 |

OTHER PUBLICATIONS

Augustin et al., "Milk Protein-Based Microencapsulated Bioactives for Improving the Nutritive Value of Food," *IDF World Dairy Summit*, Capetown, South Africa, Nov. 4-8, 38 pages, 2012.
Gunasekaran et al., "Use of Whey Proteins for Encapsulation and Controlled Delivery Applications," *Journal of Food Engineering* 83(1):31-40, 2007.
Oliver and Augustin, "Using Dairy Ingredients for Encapsulation," Chapter 22, entitled "Using Dairy Ingredients for Encapsulation," pp. 565-588 *In Dairy-Derived Ingredients: Food and Nutraceutical Uses*, 2009.
Serp. D., et al. "Characterization of an encapsulation device for the production of monodisperse alginate beads for cell immobilization," *Biotechnol Bioeng*. Oct. 5, 2000;70(1):41-53 Only two (2) pages of the Abstract.
Moiety Definition Merriam-Webster 2018, 9 pages.
Bowen, "Particle Size Distribution Measurement from Millimeters to Nanometers and from Rods to Platelets," *Journal of Dispersion Science and Technology*, 239(5):631-662, 2002.

* cited by examiner

*Primary Examiner* — Jeanette M Lieb
(74) *Attorney, Agent, or Firm* — Occhiuti & Rohlicek LLP

(57) ABSTRACT

A microcapsule includes an active component encapsulated within a polymerized hydrolyzed protein shell. The microcapsule has an average diameter that is less than one hundred micrometers as determined by a laser diffractometer.

24 Claims, 12 Drawing Sheets

A

B

C

ACTIVE COMPONENT ENCAPSULATED, PROTECTED AND STABILIZED WITHIN A PROTEIN SHELL

CROSS-REFERENCE TO RELATED APPLICATIONS

This application is a divisional application of U.S. patent application Ser. No. 14/897,901, filed on Dec. 11, 2015, which is a National Stage of International Application No. PCT/EP2014/062154, filed on Jun. 11, 2014, which claims the benefit of the Jun. 12, 2013 priority date of European Application No. 13171757.1, the contents of which are herein incorporated by reference.

FIELD OF DISCLOSURE

This disclosure relates to microcapsules comprising an active component encapsulated within a protein shell, and comestible products, especially sports nutritional products, comprising such microcapsules.

BACKGROUND

Creatine is recognized as a dietary supplement capable of increasing muscle mass and muscle performance. It is provided in a number of different forms, the most common of which is a powder that comprises creatine monohydrate.

The ergogenic effect of creatine has been a subject of systematic investigation. Most of these studies have demonstrated significant positive effects of creatine on muscle mass, muscle power, lean body mass, and performance at maximum short-duration muscle exertion in various types of sports. Today, creatine monohydrate is the most significant nutrition supplement in sports.

Known forms of creatine monohydrate lack long-term stability in water. Such forms must be made up shortly before being ingested. Such a product therefore cannot be stored during the day.

In addition to creatine itself, namely creatine monohydrate, numerous creatine salts such as creatine ascorbate, citrate, pyruvate and others have proven to be suitable nutritional supplements.

Uptake of creatine from the intestine and transport into the muscles is controlled by an NaCl-dependent creatine transporter. This uptake can promoted by the simultaneous intake of carbohydrates and proteins. It has therefore been found that in comparison with sole intake of creatine, that the combination of creatine and carbohydrates can lead to a 60% greater rise in creatine content in the muscle.

One formulation for enhancing creatine transport includes an IGF-1 modulating substance, such as particular proteins, colostrum, and recombinant IGF-1.

Despite its undisputed ergogenic and physiological effects, creatine monohydrate suffers from a number of limitations. These include low solubility and/or hydration capacity and poor stability in aqueous solutions. In addition, relatively large doses are required to elicit an ergogenic effect in the body.

Since creatine lacks marked stability in water or corresponding aqueous solutions, creatine cycling by elimination of water will generate creatinine. The rate of cycling depends on the solution's pH and its temperature. Intestinal concentration does not play any role in this process. Conversion to creatinine proceeds rapidly, in particular in the acidic pH range between three and four. The rapid breakdown of creatine in this medium virtually rules out the use of aqueous or moist formulations for human and animal nutrition. For example, based on the stomach pH alone, a significant breakdown of creatine to creatinine can occur depending on the residence time.

SUMMARY

The disadvantages of the prior art with regard to creatine solubility and stability in aqueous solution and subsequent uptake from the intestine and transport into the target tissue give rise to the object of the invention of providing encapsulated preparations of creatine. Encapsulation provides better protection for creatine than previously demonstrated. This, in turn, helps avoid breakdown of creatine to creatinine and therefore improved creatine uptake from the intestine.

An important factor is the optimum uptake and thus retention of the creatine in the target tissue. A further object of the invention is to ensure that the creatine absorbed from the intestine is optimally taken up into the target tissue rather than being excreted via the kidneys or being converted into creatinine, which is useless to the body and must likewise be excreted from the body via the kidneys. Therefore the encapsulated systems have acceptable organoleptic properties with improved bioavailability for food and beverage applications.

The majority of creatine in the human body is in two forms: the phosphorylated form, which makes up 60% of the stores, and the free form, which makes up 40% of the stores. The average 70-kilogram young male has a creatine pool of around 120-140 grams. This varies between individuals depending on the skeletal muscle fiber type and quantity of muscle mass. The endogenous production and dietary intake matches the rate of creatinine production from the degradation of phosphocreatine and creatine at 2.6% and 1.1% per day respectively. In general, oral creatine supplementation leads to increased creatine levels within the body. Creatine can be cleared from the blood by saturation into various organs and cells or by renal filtration.

Three amino acids (glycine, arginine, and methionine) and three enzymes (L-arginine: glycine amidinotransferase, guanidinoacetate methyltransferase, and methionine adenosyltransferase) are involved in creatine synthesis. The impact creatine synthesis has on glycine metabolism in adults is low. However the demand is more appreciable on the metabolism of arginine and methionine.

Creatine ingested through supplementation is transported into the cells exclusively by CreaT1. However, there exists another creatine transporter, namely CreaT2, that is primarily active and present in the testes.

Creatine uptake is regulated by various mechanisms, namely phosphorylation and glycosylation as well as extracellular and intracellular levels of creatine. CreaT1 has been shown to be highly sensitive to the extracellular and intracellular levels being specifically activated when total creatine content inside the cell decreases.

In addition to cytosolic creatine, there exists a mitochondrial isoform of CreaT1 that allows creatine to be transported into the mitochondria. This intra-mitochondrial pool of creatine appears to play a role in the phosphate-transport system from the mitochondria to the cytosol. Myopathy patients have demonstrated reduced levels of total creatine and phosphocreatine as well as lower levels of CreaT1 protein, which is thought to be a major contributor to these decreased levels.

In a first aspect, the invention features a process for producing microcapsules. Such microcapsules comprise an active component encapsulated within a polymerized hydrolyzed protein matrix. The method includes the steps of providing a suspension of hydrolyzed protein and an active component in a liquid ester, treating the suspension to generate droplets of the suspension, and immediately curing the droplets by immersion in a basic curing solution. The ester in the suspension reacts with the basic curing solution to release a salt that polymerizes the hydrolyzed protein, thus encapsulating the active component. As used herein, a "basic" solution is one with a pH that exceeds seven.

Microcapsules formed according to the process described herein are surprisingly stable upon prolonged storage in aqueous solution. For example, after as much as twenty-eight days of storage, creatine monohydrate encapsulated in hydrolyzed whey protein showed almost no loss in creatine concentration. Furthermore, creatinine, which is a breakdown product of creatine, was not detected at any significant levels even after twenty-eight days of storage under the same conditions. Hence, it has been possible to show that the encapsulation system is capable of stability in aqueous solutions.

As used herein, the term "active component" refers to an agent that is suitable for delivery to the gastrointestinal tract of a mammal, including pharmaceutically active agents and health food supplements including vitamins, minerals, co-factors, amino acids, and the like. Preferably, the active component is an active agent that partially or fully degrades in water or aqueous solution and that is typically at least partially insoluble in water.

Examples of such active agents include creatine moieties (for example creatine and its esters), beta-alanine, and amino acids, especially L-amino acids such as L-leucine, L-glutamine and the branched-chain amino acids typically comprising of leucine, isoleucine, and valine. The active agent described herein can comprise of one or more amino acids, which the body metabolizes in the stomach and intestines. The active agent can comprise one or more of the following amino acids: isoleucine, alanine, leucine, phenylalanine, threonine, tryptophan, glycine, valine, proline, histidine, serine, tyrosine, glutamate, glutamic acid, and glutamine, in any form for example as salts, esters, branched-chain amino acids, complexes, precursors, or derivatives.

In some embodiments, the active component comprises a creatine moiety, for example creatine, or a creatine precursor or derivative, examples of which include creatine monohydrate, guanidinoacetic acid (a direct precursor of creatine), creatine esters, creatinol, creatinol O-phosphate, or a mixture of at least two of these compounds. Other creatine precursors include guanidinoacetic acid, creatine esters, creatinol and creatinol O-phosphate, which are known to be converted into creatine in the body, are suitable encapsulation candidates for this specific delivery action.

The active component is preferably selected from a creatine moiety, L-Glutamine, Beta-alanine, L-Leucine or a branched-chain amino acid, or derivatives or pre-cursors thereof. These amino acids are consumed by a large number of athletes and those interested in sports nutrition for a variety of reasons, such as muscle mass gain, muscle recovery and increased energy. The vast majority of Glutamine, Leucine and Beta-Alanine in nutritional products is in the L conformation. Industry experts recommend consumption of glutamine as a powder or capsule due to instability in water and losses of the amino acids during digestion processes.

Leucine, along with isoleucine and valine, is one of the branched-chain amino acids, which play an important role in sports nutrition. Leucine is an essential amino acid and as such cannot be synthesized in the body. It must therefore be derived from the diet. Hence, leucine stability and bioavailability are vital. Generally speaking, branched-chain amino acids make up 15% of a consumed protein. Even in high protein diets, levels of branched-chain amino acids consumed, including levels of leucine, may be low. This compromises bioavailability during gastric transit. The ingredient is stable under ambient conditions; however the effect of gastric transit on free-form leucine results in poor absorption in the mammalian system.

Glutamine is an amino acid and is not recognized as essential due to the body's ability to synthesize it. As the most abundant amino acid in the body, it constitutes a little more than five percent of the amino acids found in animal-derived protein sources, such as meats, dairy, and eggs. The amino acid is consumed by a large number of athletes and those interested in sports nutrition for a variety of reasons such as muscle mass gain, muscle recovery, and increased energy.

Industry experts recommend consumption of glutamine as a powder or capsule due to stability issues with the glutamine in water. For this reason it is recommended that consumers avoid products such as pre-made drinks and bars containing the free amino acid. Regardless of the form, up to 90 percent of ingested glutamine is eliminated during digestion due to lack of protection against digestive conditions. A fraction of consumed glutamine will survive beyond the liver due the action of digestive enterocytes and immune cells within the gut.

Beta-alanine is a nutritional supplement widely used by athletes and bodybuilders to improve performance. This nonessential amino acid occurs naturally in the body and is also found in foods such as chicken, beef, pork and fish. Beta-alanine is the rate-limiting precursor of carnosine (EFSA), which potentially generates intramuscular carnosine and improved muscular endurance. Beta-alanine can be generally provided as either a powder or in gelatin capsules and its presence in foodstuffs can be measured by established methods (EFSAS). General dosage is 1.6-6.4 grams of beta-alanine per day for 4 weeks. However, an issue for beta-alanine is parenthesis, i.e., a sensation of pins and needles, that (pins and needles feeling. that occurs when administered in a large dose. An encapsulation-delayed release strategy could benefit the consumer and manufacturers by alleviating this issue. Indeed, one manufacturer recommends consuming 3.2 grams per day but breaking this amount into two to three doses per day. A delayed release formulation would add convenience to this product.

For this reason, these amino acids and branched-chain structures are suitable candidates for this formulation and delivery using the methods and products described herein. When the aforementioned sources are added to ready-to-consume supplements it is usually in a peptide-bound form, such as glycyl-L-glutamine hydrate. Hence the amount of active component per serving is ultimately limited and restricted. Regardless of the form, on average, up to ninety-two percent of ingested active agents are eliminated during digestion. A fraction of consumed active agents survives beyond the liver due the action of digestive enterocytes and immune cells within the gut. In this manner, glutamine, beta-alanine, L-leucine and branched-chain amino acids structure should be regarded as particularly preferred amino acid sources.

In some embodiments, the suspension comprises an extract of *Piper nigrum* L, i.e., black pepper, or *Piper longum* L, i.e., long pepper. Among these embodiments are those in which the extract comprises 95% piperine, hereafter referred to as "pepper extract." In such embodiments, polymerization of the hydrolyzed whey protein encapsulates the active component and the pepper extract. In some embodiments, the extract is bioperine.

Incorporation of the pepper extract into the microcapsules enhances the absorption efficiency of the active component within the gastrointestinal tract, especially when the active component is a creatine moiety, such as creatine monohydrate. The encapsulation system protects creatine better from conversion to creatinine in the stomach than known methods. The presence of pepper extract in the encapsulation matrix leads to a surprising improvement in uptake from the intestine. This, in turn, translates into distinctly higher bioavailability and thus better uptake into the target tissue.

In this structural format, creatine that has been encapsulated and stabilized by whey protein and black-pepper extract is further incorporated into the encapsulation matrix to aid creatine bioavailability in the blood. In a preferred embodiment, the combination of creatine monohydrate, whey protein, and phosphate and black-pepper extract further enhances creatine encapsulation efficiency to greater than 99.5%. This leads to enhanced creatine bio accessibility for muscle contraction and exercise.

Preferably, the encapsulation system, i.e., the suspension, has a pH value between 3 and 6 and ideally between 3.5 and 4.8. The preferred initial carrier system is a mixture of an alcohol, acetic acid, and hydrolyzed protein, with a protein of dairy origin being preferred. The amount of ester produced may be freely selected over a wide pH range, the preferred ratio being set at the selected pH value of the formulation, which is established at a pH of between three and six and preferably with pH above four. A particularly useful pH is 4.8.

If the mixture ratio is correctly selected, namely if the ratios of alcohol, acid, and protein are correct, there is virtually no restriction on the amount of salt that can be released from the ester reaction for further encapsulation purposes. For instance, when a 1:1 mixture is used, a pH value greater than four is inevitably established, this being independent of the total amount of alcohol introduced.

The foregoing technique provides a pH value acceptable from an organoleptic aspect while providing surprisingly good protection of creatine from the influence of acids, and in particular, from gastric acid. This helps to avoid the conversion of creatine to creatinine. The action of the encapsulation process could not have been predicted in the claimed pH range.

An unexpected result of the encapsulation process described herein is one that goes well beyond reduced breakdown of creatine in the stomach. Surprisingly, the process also results in improved uptake of creatine by the cells themselves. It has accordingly been possible to demonstrate that the methods and compositions described herein lead to a distinctly greater rise in creatine concentrations in the target tissue when compared with creatine monohydrate that has not been encapsulated.

The use of sodium acetate salt in connection with a pepper extract, such as bioperine, has demonstrated a surprisingly significant influence on the bioavailability and uptake of creatine into cells.

Using the encapsulation process as described herein stabilizes creatine against acids and thus reduces the breakdown of creatine in the stomach. Moreover, the presence of pepper extract improves the uptake of creatine into the cells. Sodium ions of the acetate buffer further assist uptake.

Typically, the active component is a creatine moiety. This means a molecule or complex comprising creatine, for example a creatine complex such as creatine monohydrate, or a creatine derivative or precursor such as guanidinoacetic acid, which is a direct precursor of creatine), creatine esters, creatine salts, creatinol, creatinol O-phosphate, or mixtures of at least two of these compounds. Examples of creatine salts include creatine hydrochloride and creatine nitrate. However, the process described herein is also applicable to the encapsulation of other active components, especially active components, for oral delivery. Examples include glutamine, oil-soluble bioactive agents, such as vitamins and minerals, fatty acids, and fat-soluble colors or flavors.

In some practices, the process includes an initial step in which the ester is formed in-situ, typically by reaction between an alcohol, preferably a weak alcohol, and an organic acid, preferably a weak organic acid, in the presence of the hydrolyzed protein and/or the active component.

In one embodiment, the suspension comprises a phosphate moiety suitable for crosslinking hydrolyzed-protein in the formed microcapsules. This embodiment is particularly suitable when the active agent is a creatine moiety. The phosphate moiety may be, for example, a phosphate salt, such as disodium phosphate. This structural addition of phosphate cross-linkers into the extrusion matrix enhances immediate creatine absorption and metabolism and potentially enables the accelerated generation of high-energy molecules, such as ATP, during exercise and creatine loading. In some embodiments, the phosphate is added to the suspension at a concentration of 0.01M to 0.05M, typically about 0.01M to 0.03M, and ideally about 0.02M.

In a preferred embodiment, the suspension is formed by mixing the active component, acetic acid, a weak alcohol, and hydrolyzed protein together to form a suspension of hydrolyzed protein and active component in an acetate ester.

A preferred embodiment features forming the suspension by mixing a creatine moiety, for example, creatine monohydrate, acetic acid, a weak alcohol, and hydrolyzed protein together to form a suspension of hydrolyzed protein and the creatine moiety in an acetate ester.

As used herein, the term "hydrolyzed" means that the protein has been treated with protease enzymes to at least partially digest native protein.

In some embodiments, the hydrolyzed protein has a degree of hydrolysis of 18-85%. The "degree of hydrolysis" is defined as the proportion of cleaved peptide bonds in a protein hydrolysate. The degree of hydrolosis is determined using the OPA spectrophotometric assay, which involves using N-acetyl-L-Cysteine (NAC) as the thiol reagent.

Preferably, the hydrolyzed protein is hydrolyzed whey protein, ideally hydrolyzed whey protein obtained from milk, especially bovine milk. However, other types of hydrolyzed protein may be employed including, for example, bovine collagen, pea, rice or non-whey milk proteins.

A hydrolyzed protein of choice would be from a dairy source ingredient with 90-95% protein (w/w) protein content. The ideal ratio for milk proteins β-lactoglobulin and α-lactalbumin would be 3:1 to 5:1. In some preferred embodiments, the ratio is approximately 4:1. In yet other preferred embodiments, the ratio is 85:15.

Flavourzyme represents an ideal enzyme for hydrolysis of dairy proteins. Flavourzyme is a protease-peptidase complex produced by submerged fermentation of a selected strain of Aspergillu oryzae, as produced by Novo Nordisk A/S.

A preferred embodiment uses Flavourzyme as standardized in terms of leucine amino peptidase units (LAPS) by the manufacturer. Hydrolysates used herein are prepared using a measure amount of Flavourzyme with 1000 LAPU with defined hydrolysis conditions. Temperatures can be within the range of 35-65° C., preferably, 40-60° C., ideally 45-50°

C. pH values can be within the range 4-9, preferably, 5-8, ideally 6.5-7.5. Hydrolysis is performed with an enzyme/substrate ratio (E/S) of 1/200, preferably, 1/150, ideally 1/100, on the basis of total protein content.

The step of treating the suspension to generate droplets may be carried out by extrusion. Some embodiments combine extrusion with a break-up technique, such as liquid-jet break up. Such methods may be carried out using an encapsulator.

However, it is also possible to generate the droplets by other techniques including spray drying and spray chilling. All of these techniques generate droplets of suspension in a stable format, i.e., with little or no polymerization of hydrolyzed protein. These droplets are immediately immersed in the basic curing bath.

A typical suspension comprises hydrolyzed protein, a phosphate moiety, and pepper extract in a liquid ester base. A suitable protein is whey protein.

In some embodiments, the basic curing solution for formation of microcapsules contains glycerol, preferably in an amount of 0.01 to 0.10M, and ideally in an amount of 0.04 to 0.07M. This has been found to reduce surface tension during formation of droplets and capsules. The presence of glycerol in the basic curing solution results in glycerol being contained in the microcapsule membrane, typically in an amount of about 0.05% glycerol. This results in microcapsules with a satisfactory spherical shape and a satisfactory size of between twenty and one hundred fifty microns.

In some embodiments, the presence of glycerol reduces surface tension during capsule formation and further contributes to enhanced creatine encapsulation efficiency, for example with an approximately 14.5% enhanced creatine yield.

Furthermore, glycerol incorporation into creatine microcapsules has the potential to further enhance water-holding capacity and fluid retention in the muscle during creatine absorption phase.

In a preferred embodiment, the presence of glycerol within the encapsulation matrix promotes hydration and regeneration of muscle. The methods and compositions described herein highlight the need to include glycerol within the encapsulation matrix in the presence of whey protein to ensure optimum encapsulation efficiency and to further aid muscle fluid retention during and after creatine absorption.

In another aspect, the invention features a method for producing microcapsules that comprise an active component encapsulated within a polymerized hydrolyzed protein matrix. Such a method includes providing a suspension of hydrolyzed protein and an active component in a liquid ester, treating the suspension to generate droplets of the suspension, and immediately curing the droplets by immersion in a basic curing solution. The ester in the suspension reacts with the basic curing solution to release a salt that polymerizes the hydrolyzed protein, thereby encapsulating the active component. The basic curing solution comprises glycerol in an amount of 0.04%-0.07% (v/v).

In some embodiments, generating droplets includes generating droplets having a core and a coating. The core comprises the suspension and the coating comprises hydrolyzed protein in a liquid ester.

One method of generating such droplets comprises using an extruder having concentric nozzles in which the inner nozzle extrudes a core-forming stream and the outer nozzle extrudes the coating-forming stream. In this method, the active agent is contained within the core. The hydrolyzed protein in the coating is polymerized when the droplets are immersed in the basic curing solution. This particular method is suitable for generating microcapsules in which the suspension comprises a non-aqueous base such as an emulsion of oil and water. An example of such a base is one that comprises a lipid-soluble component. In such methods, the suspension additionally comprises the fat-soluble component and a suitable dispersing agent, such as a fatty acid.

In one embodiment, the suspension comprises astaxanthin, which as used herein is identified by CAS Number 472-61-7. The addition of astaxanthin into the suspension further enhances capsule longevity and shelf-life and possibly enhances muscle total creatine content as compared to the ingestion of creatine monohydrate alone. In some embodiments, the presence of astaxanthin in whey protein encapsulation matrices provides an additional protective barrier against water. This further protects creatine by retarding its degradation into creatinine.

In the presence of an astaxanthin-hydrolyzed protein formulation/suspension, a dispersing agent (i.e., fatty acid) must be added to assist the dissolution of astaxanthin with hydrolyzed protein. This dispersing agent is preferably an oil-based agent, for example a fatty acid, for example lipoic acid or palmitic acid.

The addition of astaxanthin in an oil-based agent, such as lipoic acid or palmitic acid, will optimize the homogenous dispersion of astaxanthin throughout the encapsulation matrix. In some embodiments, the addition of astaxanthin using an oil-based agent, such as lipoic acid, to the encapsulation formulation potentially maximizes creatine uptake by the human skeletal muscle when creatine monohydrate is ingested in an encapsulated form, as outlined above.

Thus, in one embodiment, the suspension comprises hydrolyzed protein, ideally hydrolyzed whey protein, an active agent, pepper extract, and astaxanthin dissolved in a dispersing agent.

In another embodiment, the suspension comprises hydrolyzed protein, ideally hydrolyzed whey protein, an active agent, pepper extract, a phosphate moiety, and astaxanthin dissolved in a dispersing agent.

The subject matter described herein has the potential to significantly improve creatine protection against stomach acid, due to the presence of whey protein matrices, to augment creatine absorption, due to the presence of black-pepper extract and astaxanthin oil-based dispersions, and to enhance creatine uptake and retention in the muscle, assisted by the presence of glycerol for enhanced ergogenic performance, bioavailability and bioaccessibility, possibly catalyzed by the presence of phosphate.

Thus, in a preferred embodiment, the subject matter described herein provides a way to produce microencapsulates comprising an active component, preferably a creatine moiety, that is encapsulated within a polymerized hydrolyzed protein shell, which is preferably a polymerized hydrolyzed whey protein shell.

Such a method includes mixing an organic acid, an alcohol, hydrolyzed protein, and an active component to generate a suspension of hydrolyzed whey protein and the active component in a liquid ester carrier; treating the suspension to generate an aqueous formulation with addition of a phosphate moiety, a pepper extract, or both; and treating the aqueous formulation to generate droplets and immediately immersing the droplets in a basic curing solution. The ester reacts with the basic curing solution to release a salt that polymerizes the hydrolyzed whey protein encapsulating the active component in the presence of the pepper extract, the phosphate moiety, or both.

In another aspect, the invention features a method for producing microcapsules comprising an active component, preferably a creatine moiety, encapsulated within a polymerized hydrolyzed protein shell, preferably a polymerized hydrolyzed whey protein shell. Such a method includes mixing an organic acid, an alcohol, hydrolyzed protein, and an active component to generate a suspension of hydrolyzed whey protein and the active component in a liquid ester carrier; treating the hydrolyzed protein suspension to generate an emulsion, with addition of astaxanthin, and optionally one or more of a phosphate moiety, and pepper extract, and emulsified in the presence of a dispersing agent; treating the emulsion to generate droplets and immediately immersing the droplets in a basic curing solution optionally containing additional phosphate and glycerol. The ester reacts with the basic curing solution to release a salt that polymerizes the hydrolyzed protein, encapsulating the active component in the presence of astaxanthin and lipoic acid, and optionally pepper extract, a phosphate moiety or both.

In the above practice, the droplets that are generated comprise a core and a coating. This can be achieved using concentric nozzles in which the emulsion is extruded through an inner nozzle and a coating formulation, preferably comprising hydrolyzed protein in a liquid ester, and optionally a phosphate moiety, is extruded through the outer nozzle. The coating formulation may also comprise the emulsion. The coating formulation must comprise hydrolyzed protein in a liquid ester, but preferably does not comprise the active agent.

Preferably, the process has an encapsulation efficiency of between 92% and 98% as determined using the following equation: Encapsulation efficiency (%)=((total loading creatine−creatine losses)/total loading creatine)×100

In some practices, the process employs creatine monohydrate, typically crystalline creatine monohydrate. Ideally, the crystalline creatine monohydrate has a prismoidal topography. In some of these practices, the creatine monohydrate is spray-dried creatine monohydrate. Among these are practices that include spray drying to form crystalline creatine monohydrate, typically at low temperature, an aqueous suspension of creatine monohydrate, include, as an example, a suspension of creatine monohydrate in alcohol.

Microcapsules formed according to the above-mentioned methods were preferably prepared using the co-extrusion laminar jet break-up technique (Encapsulator 1, Inotech, Switzerland). The device was fitted with an inner nozzle (ranging from 20-300 micrometers) and an outer nozzle (ranging from 300-500 micrometers. In a first formulation, this liquid ester suspension was treated with phosphate and pepper extract and supplied to the inner nozzle via sterile filtration coupled to a peristaltic pump to assist the formation of liquid-core capsules.

In an alternative practice, the liquid ester suspension is emulsified with pepper extract and astaxanthin and an oil-based agent such as alpha lipoic acid. This results in a second formulation. The first or second formulation will flow through the inner nozzle and create the capsule inner core. The outer capsule membrane is formed using the creatine liquid ester in the presence of additional phosphate, which is supplied to the outer nozzle using an air pressure regulator that enables flow rates ranging from five to ten liters per hour under no more than 0.8 bar of pressure.

Either the first or second formulation is extruded through a heated nozzle into a weak basic environment. A typical nozzle is between twenty and four hundred micrometers. A typical temperature is thirty five degrees Celsius.

At this point, the pH increases and the ester reacts with the base to release an acetate salt that instantly polymerizes the protein suspension with simultaneous encapsulation of bioperine, glycerol, phosphate, and bioactive material, e.g., creatine. If oil core capsules are produced, again, the pH will increase, thereby releasing an acetate salt that instantly polymerizes the protein suspension with simultaneous encapsulation of bioperine, glycerol, phosphate, astaxanthin, and alpha lipoic acid within the core with bioactive material, e.g., creatine.

Having chosen flow rates that enable a stable jet of creatine droplets through the nozzles, frequency and electrostatic charge were set to have a stable bead chain visible in the strobe light and a circular dispersion of the drops during their fall into a gelling bath placed fifteen centimeters under the nozzle. This gelling bath comprised 500 milliliters of di-sodium phosphate buffer in 10 mM MOPS (3-(N-morpholino)propanesulfonic acid) with 0.04-0.07% w/v glycerol, at a pH of 7.4. The bath was magnetically stirred to form a visible vortex. Droplet immersion of creatine into this curing solution causes the instantaneous release of the acetate salt that polymerizes the hydrolyzed protein. This further encapsulates the creatine moiety within the capsule core and outer whey protein membrane.

As a result, the first formulation generates creatine monohydrate encapsulated in the presence of phosphate, glycerol and, black pepper, surrounded by an outer membrane of hydrolyzed whey protein.

The second formulation generates creatine monohydrate encapsulated within an alpha-lipoic acid oil core in the presence of phosphate, glycerol, and black pepper, further surrounded by an outer membrane of hydrolyzed whey protein. Creatine capsules are further incubated for twenty minutes in the basic curing buffer and washed twice with 10 mM MOPS, with a final wash performed with deionized water for thirty minutes.

As used herein, the term "microcapsule" refers to a particle comprising an active component encapsulated within a hydrolyzed protein shell and having an average diameter of less than a hundred micrometers, ninety micrometers, eighty micrometers, seventy micrometers, sixty micrometers, and fifty micrometers. Preferably, the microcapsule has an average diameter of less than fifty micrometers, forty micrometers, thirty micrometers, or twenty micrometers. The method of measuring average diameter and D (v, 0.9) (size at which the cumulative volume reaches 90% of the total volume), of micro-capsules is determined using a laser diffractometer, such as the Mastersizer 2000 manufactured by Stable Micro Systems, Surrey, UK, with a range of 0.2-2000 micrometers. For particle size analysis, micro-bead batches were resuspended in an ultra-pure water, such as MILLI-Q water, and size distribution was calculated based on the light intensity distribution data of scattered light.

The term "protein gel" as used herein should be understood to mean a sol in which the solid particles are meshed such that a rigid or semi-rigid mixture results. The ridigity of the gel structure will be determined by a texture analyzer, such as the TA.XT analyzer. A gel is placed under a probe and, by running a test, is compressed at 0.3 millimeters per second until it collapses. The force, in grams, and the distance, in millimeters, are measured and give the mechanical strength of the gel. The process is repeated four to six times to ensure accuracy. The strength of one gel can be calculated by dividing the strength measured by the calculating the surface area of the gel particle under the probe.

In some embodiments, the suspension comprises 10-25% or 10-20% hydrolyzed protein (w/v).

In some embodiments, the suspension comprises 75-90% or 80-90% active component (w/v).

In other embodiments, the suspension further comprises 0.01-0.05% pepper extract (w/v); 0.02-0.5 M phosphate moiety; 0.03-0.08% astaxanthin (w/v); and 0.6-0.9% dispersing agent (w/v).

In yet other embodiments, the suspension comprises 10-25% hydrolyzed protein (w/v); 75-90% active component (w/v); 0.01-0.05% pepper extract (w/v); 0.02-0.5 M phosphate moiety; 0.03-0.08% astaxanthin (w/v); and 0.6-0.9% dispersing agent (w/v).

In still other embodiments, the suspension comprises: 10-20% hydrolyzed protein (w/v); 80-90% active component (w/v); 0.01-0.05% pepper extract (w/v); 0.02-0.5 M phosphate moiety; 0.03-0.08% astaxanthin (w/v); and 0.6-0.9% dispersing agent (w/v).

In still other embodiments, the hydrolyzed protein is hydrolyzed whey protein.

In some embodiments, the active agent is a creatine moiety.

In some embodiments, the pepper extract is bioperine.

In some embodiments, the dispersing agent is a fatty acid.

In some embodiments, the dispersing agent is alpha-lipoic acid.

In some embodiments, the suspension comprises: 0-20% hydrolyzed whey protein (w/v), 80-90% creatine moiety (w/v), 0.025-0.035% bioperine (w/v), 0.03-0.04 M phosphate moiety, 0.04-0.06% astaxanthin (w/v), and 0.7-0.85% alpha-lipoic acid.

The term "liquid ester" should be understood to mean an ester of an organic acid in a liquid form.

In some embodiments, the process includes an initial step in which the ester is formed in-situ. Among these are embodiments in which it is formed by reaction between an alcohol and an organic acid.

Practices include those in which the alcohol is a weak alcohol and those in which the organic acid is a weak organic acid.

Also included are practices in which the step is carried out in the presence of the hydrolyzed protein and/or the active component.

The term "weak alcohol" should be understood to mean any of a large number of colorless, flammable organic compounds that contain the hydroxyl group (OH) and that slowly form esters with acids. Simple alcohols, such as methanol and ethanol, are water-soluble liquids, while more complex ones, like acetyl alcohol, are waxy solids. Names of alcohols usually end in "ol." Typical alcohol concentrations range from 0.2M-0.4 M (98% purity).

Examples of weak organic acids include lactic acid, acetic acid, formic acid, citric acid, and oxalic acid.

In some embodiments, the acid is acetic acid.

An organic acid is an organic compound with acidic properties. The most common organic acids are the carboxylic acids, whose acidity is associated with their carboxyl group —COOH. Sulfonic acids, containing the group —$SO_2OH$, are relatively stronger acids. Alcohols, with —OH, can act as acids but they are usually very weak. The relative stability of the conjugate base of the acid determines its acidity. Typically, the acid has a concentration of 0.5-0.65M.

Typically, the suspension has a concentration of carboxylic ester of 0.1-0.6M, preferably 0.2-0.4M, and ideally about 0.3M.

In another aspect, the invention features a microcapsule formed according to the methods described herein.

In yet another aspect, the invention features a multiplicity of microcapsules formed according to the methods described herein.

In another aspect, the invention features a comestible item that comprises a multiplicity of microcapsules formed according to the methods described herein. Examples of such comestible items include a food product or beverage for human consumption.

In another aspect, the invention features a microcapsule comprising an active component encapsulated within a polymerized hydrolyzed protein shell. Among these are microcapsules having a diameter of less than 100 micrometers, 90 micrometers, 80 micrometers, 70 micrometers, 60 micrometers, 50 micrometers. Preferably, the microcapsules have an average diameter of less than 50 micrometers, 40 micrometers, 30 micrometers, or 20 micrometers.

Suitably, the microcapsule comprise pepper extract, ideally bioperine, encapsulated within the polymerized hydrolyzed protein shell.

Typically, the active component is a creatine moiety. As used herein, a "creating moiety" is a molecule or complex comprising creatine. Examples include a creatine complex, such as creatine monohydrate, a creatine derivative, such as creatine ethyl ester, and a creatine salt. Examples of creatine salts include creatine hydrochloride and creatine nitrate.

In some embodiments, the microcapsules comprise alternative or additional active components. Examples of alternative or additional active components include active components for oral delivery, such as glutamine, oil soluble bioactive substances, such as vitamins and minerals, fatty acids, or fat soluble colors or flavors. In some embodiments, the creatine monohydrate is crystalline creatine monohydrate. Ideally, the crystalline creatine monohydrate has a prismoidal topography (see FIG. 2A). Typically, the creatine monohydrate is spray dried creatine monohydrate, ideally crystalline creatine monohydrate obtained by spray drying (typically at low temperature) an aqueous suspension of creatine monohydrate, ideally a suspension of creatine monohydrate in alcohol.

In some embodiments, the microcapsule comprises a phosphate crosslinker, that crosslinks amino acids in the polymerized hydrolyzed protein chains.

In some embodiments, the polymerized hydrolyzed protein comprises glycerol.

In some embodiments, the hydrolyzed protein is hydrolyzed whey protein, ideally hydrolyzed whey protein obtained from milk, especially bovine milk. However, other types of hydrolyzed protein can be employed. Examples include bovine collagen, pea, rice, or non-whey milk proteins for hydrolyzing proteins.

A hydrolyzed protein of choice would be from a dairy source ingredient with 90-95% protein (w/w) protein content. The ideal ratio for milk proteins β-lactoglobulin and α-lactalbumin would be approx. 4:1, more specifically, 85:15.

Flavourzyme is a particularly good enzyme for hydrolysis of diary proteins. Flavourzyme is a protease-peptidase complex produced by submerged fermentation of a selected strain of Aspergillu oryzae, as produced by Novo Nordisk A/S. It is preferable to use Flavourzyme standardized in terms of Leucine Amino Peptidase Units (LAPS) by the manufacturer. Hydrolysates for the present invention are prepared using a measured amount of Flavourzyme with 1000 LAPU with defined hydrolysis conditions.

Preferred temperatures are within the range of 35-65° C., preferably, 40-60° C., ideally 45-50° C.

Preferred pH values are within the range 4-9, preferably, 5-8, ideally 6.5-7.5.

Hydrolysis is typically performed with an enzyme/substrate ratio (E/S) of 1/200, preferably, 1/150, and ideally 1/100, on the basis of total protein content.

In some embodiments, the microcapsules comprises 10-25% hydrolyzed protein (w/v).

In some embodiments, the microcapsule comprises 75-90% active component (w/v).

In some embodiments, the microcapsule comprises 1.0-0.5% pepper extract (w/v).

In some embodiments, the microcapsule comprises: 10-20% hydrolyzed protein (w/v), 80-90% active component (w/v), and 0.01-0.05% pepper extract (w/v). Among these are embodiments that also include a phosphate moiety.

In some embodiments, the microcapsule comprises: 10-20% hydrolyzed protein (w/v), 80-90% active component (w/v), and 0.01-0.05% bioperine (w/v). Among these are embodiments that also include one or more of a phosphate moiety, 0.04-0.07% glycerol (w/v), 0.03-0.08% astaxanthin (w/v), and 0.6-0.9% alpha-lipoic acid (w/v).

In some embodiments, the microcapsule comprises: 10-20% hydrolyzed protein (w/v), 80-90% active component (w/v), 0.01-0.05% bioperine (w/v), a phosphate moiety, 0.04-0.07% glycerol (w/v), 0.03-0.08% astaxanthin (w/v), and 0.6-0.9% alpha-lipoic acid (w/v).

Embodiments also include those in which the microcapsule is provided in the forms of powders, granular products, pastilles, capsules, and effervescent tablets, solutions and gel products have shown to be particularly suitable administration forms.

Still other embodiments use the creatine preparation in combination with other active ingredient having a physiological effect.

In some embodiments, the microcapsules are stable in water for a period of at least twenty days.

In some embodiments, the microcapsules are stable in water for a period of at least twenty-five days.

In some embodiments, the microcapsules are stable in water for a period of at least or preferably twenty-eight days.

As used herein, "stable" means that there is no detectable loss of encapsulated active agent after the time period for a 6.25% suspension of microcapsules in water, i.e., five grams of microcapsules dry weight in eighty grams of water.

In some cases, the encapsulation described herein benefits animals. Practices therefore include administration to animals. If the described creatine formulations are used as a feedstuff additive, administration should in particular be regarded as preferred for breeding and fattening animal and animals in competitive sport. The methods also include administration to horses, pigs, poultry, and fish.

In another aspect, the invention features a manufacture comprising multiplicity of microcapsules as described herein.

Embodiments include those in which the manufacture includes a comestible product, those in which it includes a comestible sports nutrition product, those in which it includes a food, those in which it includes a beverage, and those in which it includes a supplement.

Embodiments also include those in which the manufacture includes a powder, a particulate material, a unit dose product, and a tablet.

In some embodiments, the manufacture includes a beverage, including a sports nutritional beverage, that has a multiplicity of microencapsulates as described herein suspended in a liquid carrier.

In some embodiments, the manufacture comprises a snack bar, including a sports nutritional snack bar, that includes a multiplicity of microencapsulates as described herein suspended in an edible carrier.

In some embodiments in which the manufacture is a comestible product, including those in which it is a beverage and those in which it is a snack bar, the manufacture includes gelled hydrolyzed protein that has a degree of hydrolysis of less than 50%, a degree of hydrolysis of less than 40%, a degree of hydrolysis of less than 30%, and a degree of hydrolysis of less than 20%.

In some embodiments in which the manufacture is a comestible product, including those in which it is a beverage and those in which it is a snack bar, the gelled hydrolyzed protein has a degree of hydrolysis of between 80%-85%.

In another aspect, the invention features a method for making a crystalline creatine monohydrate in which crystals have a low particle size distribution and a stable crystalline structure. In some practices, the average particle size is less than 10 micrometers. This is advantageous for applications in which the crystalline creatine monohydrate is to be encapsulated.

Among other practices are those in which the crystalline creatine monohydrate has a substantially prismoidal topography. This is shown in FIG. 2A. Typically, at least 50%, 60%, 70%, or 80% (v/v) of the crystals have a particle size of 1 to 10 micrometers.

In another aspect, the invention features a method of preparing crystalline creatine monohydrate having a narrow particle size distribution. Such a method include preparing an aqueous suspension of creatine monohydrate and spray-drying the aqueous suspension to generate crystalline creatine monohydrate having a narrow particle size distribution. Typically, the spray-drying step is carried out at a low temperature range of 30-70 degrees. A preferable range is 40-60 degrees and an optimal range is 50-55 degrees.

In another aspect, the invention features a crystalline creatine monohydrate formed according to a method of the invention.

In another aspect, the invention features a non-therapeutic method of increasing athletic performance in an individual comprising the steps of administering, to the individual, a comestible product as described herein in which the active component comprises a creatine moiety, preferably creatine monohydrate, and the microencapsulates in the preparation are broken down in the gastrointestinal tract of the individual to release the active component.

These and other features of the invention will be apparent from the following detailed description and the accompanying figures, in which:

DETAILED DESCRIPTION

Figure 1:
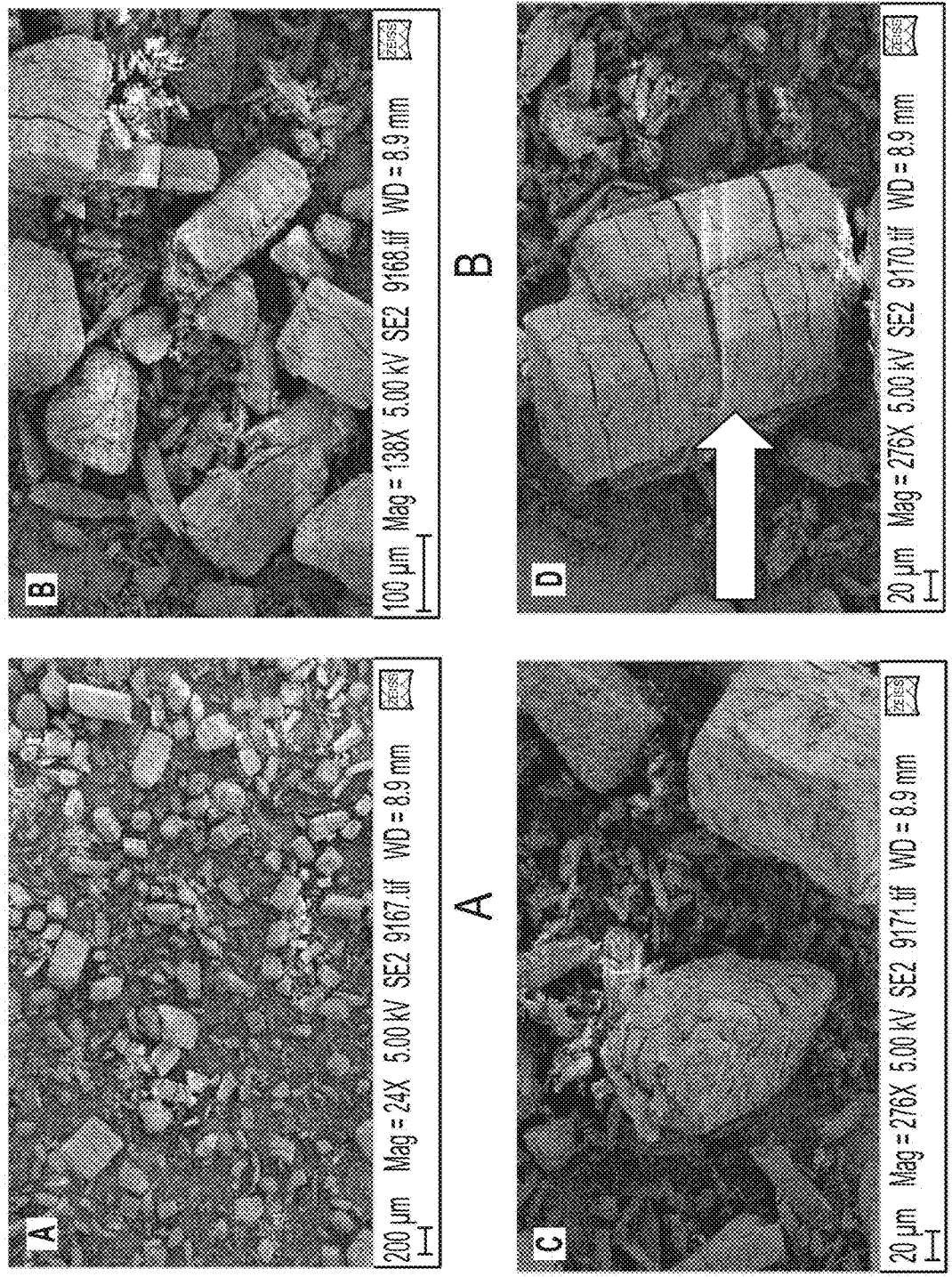
FIG. 1, which is spread across two sheets and six panels, shows scanning electron microscope images of raw creatine monohydrate.
Figure 1:
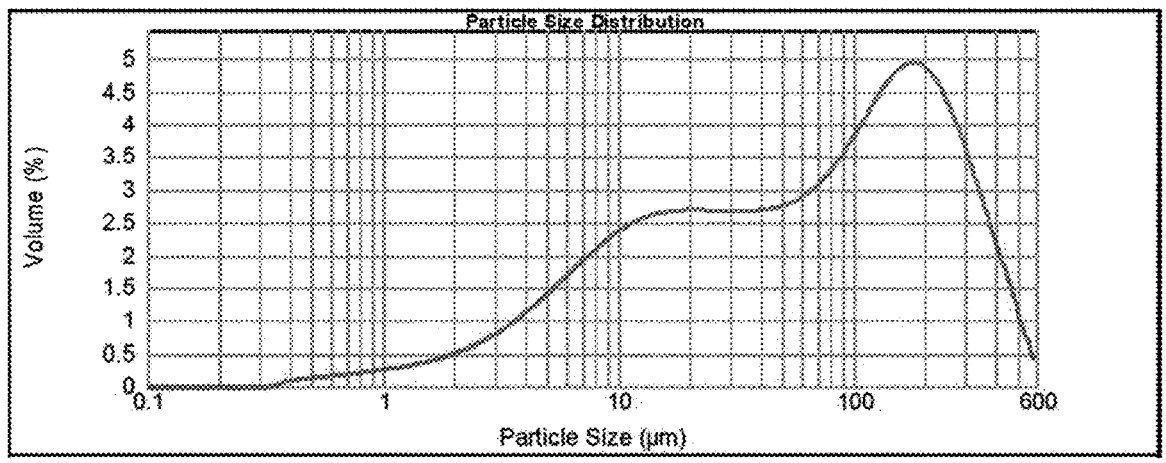

The subject matter described herein includes a method for controlling the timing of acetate-mediated polymerization of milk proteins for the encapsulation of bioactive materials, with particular interest in creatine monohydrate in the presence of black pepper extract and astaxanthin, and also for controlling the release of the encapsulated bioactive material by controlling phosphate cross-linking and digestive properties of the encapsulation system in order to enhance the absorption, uptake, and muscle utility of active creatine.

The subject matter provides a bioactive material, and in particular, creatine monohydrate, with structural features for long term stability via encapsulation of an aqueous formulation that contains milk protein, black pepper extract, bioperine, i.e., CAS:94-62-2, astaxanthin, i.e., CAS AS 472-61-7, an alcohol, and an organic acid. This combination of substrates will naturally produce an ester, which subsequently produces a salt upon reaction with a weak base. This produces a polymerized protein matrix stabilized by intra-molecular disulphide bonds. Residual alcohol generated during this reaction is subsequently removed during the drying process.

The incorporation of bioperine enhances creatine stability against stomach acid and enzymatic digestion on the luminal side of the gastro-intestinal tract. As a result of the digestibility of the hydrolyzed whey protein capsules, encapsulated creatine will be released at the proximal ileum to enable absorption and uptake of creatine into the blood stream from the luminal side. In this way, encapsulation promotes the absorption efficiency and bioavailability of creatine monohydrate.

The presence of cross-linked phosphate enables the accelerated generation of ATP during creatine administration. The presence of glycerol promotes fluid retention during exercise and muscle contraction. The incorporation of black pepper extract and/or astaxanthin in the presence of alpha lipoic acid further promotes the bio accessibility of creatine for muscles. Furthermore, the presence of hydrolyzed milk protein eliminates the allergenic nature of the final product.

The method provides mild process conditions for the production of functional and bioavailable creatine monohydrate for incorporation into a beverage. Previous inventions failed to adequately protect creatine monohydrate from heat and low pH during storage and delivery in beverage formats with added functional ingredients to enhance bioavailability in the blood and subsequent bio accessibility in the muscle.

This process for stabilization of bioactive material has the ability to combine, protect, and release functional ingredients at site-specific absorption sites in the gastro-intestinal tract to achieve synergistic ergogenic effects with enhanced hydration capacity to assist long term muscle contraction. Creatine capsules are small, i.e., less than 50 microns, mono-dispersed, homogenous, and spherically-shaped stabilized particles, with a narrow size distribution. They are produced quickly and under mild and simple encapsulation conditions at low cost and with high encapsulation efficiencies, measured as a percentage of product encapsulated, for commercial production.

The subject matter described herein includes an encapsulation process for bioactive components that uses creatine monohydrate as the test material. Aqueous suspensions are prepared for initial molecular crystallization in the presence of crosslinking agents. This is followed by extrusion encapsulation. The technology enables the production of aqueous-core capsules or oil-core capsules through incorporation of astaxanthin using an oil-based dispersing agent.

Step 1: Molecular Stabilization

Scanning electron microscopy provided a valuable tool for the visualization and ultimate optimization of the best encapsulation system for efficient delivery of bioactive materials such as creatine monohydrate. FIG. 1 shows an image of free creatine monohydrate. It is clear that the structure of raw creatine monohydrate is highly unstable as a monohydrate material.

Large particles shown in panels A-D of FIG. 1 illustrate a potential to break down into smaller particles with a greater hydration capacity. Panel D of FIG. 1 illustrates dehydration layers that typically correspond to an unstable compound. These are pointed out by the arrow. Panels E and F of FIG. 1 illustrate the unfavorable broad size distribution of commercially available creatine monohydrate.

Particle sizes ranged all the way from a few microns to over six hundred microns. This was not acceptable for either stability or for further encapsulation. Hence, before initiating encapsulation, it was imperative to generate creatine with a more even distribution of sizes and a stable crystal structure.

To achieve the foregoing, creatine monohydrate was spray-dried using pharmaceutical-grade ethanol at lower temperatures. This maintained the functional attributes of creatine. Following spray-drying, the creatine produced was assessed for suitable size distribution and for its crystal structure.

Figure 2:
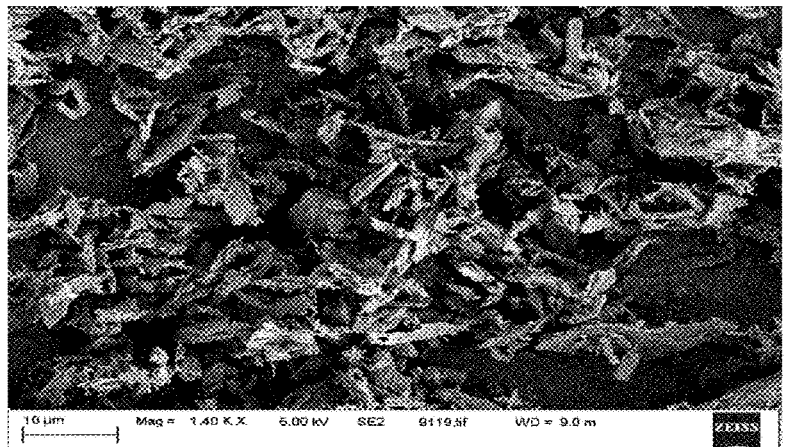
FIG. 2 shows creatine monohydrate after spray drying in the presence of pharmaceutical grade ethanol.
Figure 2:
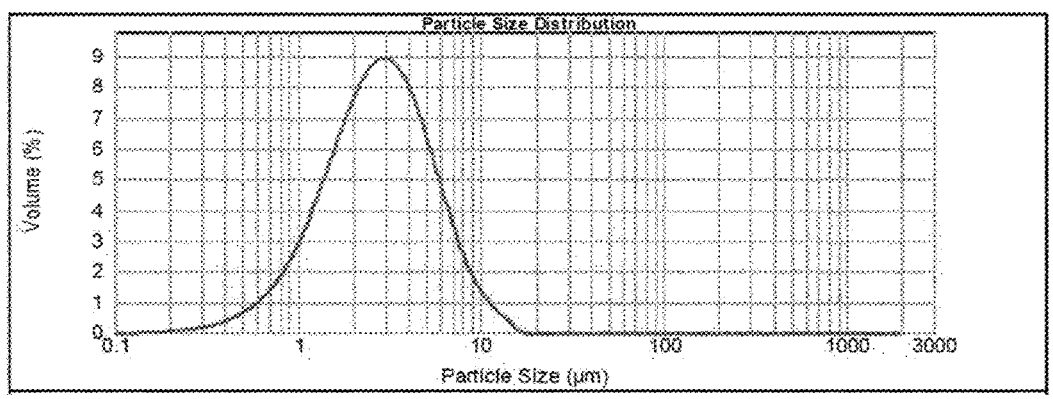

Panel A in FIG. 2 shows prismoidal creatine. This prismoidal form ultimately generates a crystal with a large surface area. A large surface area promotes bonding with the encapsulation polymer. The creatine shown is suitable for encapsulation because the particle sizes are less than ten microns.

Step 2: Encapsulation

Production of Aqueous Encapsulation Systems:

Micro-dispersed whey protein microcapsules were prepared based on laminar jet break-up for the generation of whey protein micro-capsules loaded with creatine monohydrate and bioperine. Liquid ester carrier was delivered to a nozzle via a feed line. The nozzle had a diameter that was between twenty and one thousand micrometers. A PTFE membrane connected the nozzle to a vibrating device. The vibrating device was insulated from the surrounding structures by rubber mounts to avoid the generation of resonance frequencies in the system.

The method includes preparing an aqueous formulation. Such a formulation includes the bioactive material (i.e., creatine monohydrate), milk protein, a pharmacological agent (i.e., a weak alcohol), and an organic acid (i.e., acetic acid). This combination of substrates naturally produces an acetate ester that is stable at room temperature. However, no salt is present to initiate protein polymerization. Therefore, the suspension remains in a fluid state.

In a first formulation, the creatine liquid ester is treated with phosphate and black-pepper extract and fed to the nozzle via sterile filtration coupled to a peristaltic pump to assist the formation of aqueous capsules. The protein-creatine-ester blend is aseptically extruded through the assigned nozzle to generate a steady stream of droplets regulated by air pressure enabling flow rates ranging from ten to fifteen liters per hour under a pressure of no greater than 0.6 to 0.8 bar.

After having chosen flow rates to generate a stable jet of droplets through the nozzles, the next step is to set frequency and electrostatic charge to cause formation of a stable bead chain visible in a strobe light and a circular dispersion of drops during falling into a gelling bath. The gelling bath comprised an alkaline phosphate buffer (0.4M) placed fifteen centimeters under the nozzle. The basic gelling bath was continuously agitated to avoid coalescence or flocculation of microcapsules during curing.

Some practices include inducing charge on the mononuclear droplets to promote their dispersion and to prevent coalescence from occurring in the air and/or upon impact. Such coalescence would result in formation of droplets and/or larger gelled particles. The charge is applied at values ranging between 0.8-1.1 millivolts.

Upon landing in the phosphate gelling bath, high surface tension may retard droplet movement. This retardation can result in gelled particles having irregular shapes. In some instances this delay can cause the droplet to burst. This would release the creatine liquid ester carrier before encapsulation takes place.

To avoid this difficulty, it was useful to reduce surface tension by adding surfactant and/or by slightly heating the phosphate solution, for example to a temperature that is between fifty and sixty degrees Celsius. Doing so permitted a drop to enter the solution more quickly, thereby reducing a risk of its deformation and promoting immediate encapsulation.

For this reason, it was important to include glycerol in the phosphate gelling bath with a temperature of thirty-five degrees Celsius. The presence of glycerol in the gelling bath also resulted in glycerol being incorporated into the final creatine capsule. Due to the fact that glycerol has favorable hydration properties for muscle function, the inclusion of glycerol in the encapsulation system comes with its own functional and ergogenic benefit.

The gelling bath comprised five hundred milliliters of di-sodium phosphate buffer in 10 mM MOPS with 0.04-0.07% w/v glycerol, 0.6-0.9% (w/v) alpha lipoic acid at a pH of 7.4. The bath was magnetically stirred to form a visible vortex. Droplet immersion of creatine into this curing solution caused the instantaneous release of acetate salt, which in turn polymerized the hydrolyzed protein, which further encapsulated the creatine moiety within the gelled structure in the presence of black pepper extract phosphate and glycerol.

During jet break-up and/or when entering the gelling bath, a high negative charge was induced onto the droplet's surface using an electrical potential of 0-2.15 kV between the nozzle and an electrode that was placed directly underneath the nozzle. As creatine droplets fell through the electrode, they were deflected from their vertical path. This promoted droplet impact over a larger area in the gelation solution. This enabled mono-disperse capsules with a standard size deviation of less than ±1.5% to be generated.

Within the gelling bath, several instantaneous reactions occurred. When the droplet entered the gelling bath, the pH increased and the ester reacted with the base to release an acetate salt that quickly polymerized the protein suspension with simultaneous encapsulation of bioperine, glycerol, phosphate and bioactive material, such as creatine. This reaction produced residual amounts of alcohol. This alcohol was subsequently removed during the final drying process to alleviate any difficulties associated with alcohol in food.

Pliable micro-beads were cured and/or polymerized at room temperature in the phosphate buffer, recovered, and then washed twice in sterile water. Matrix characterization was then performed as a function of cure time in buffer, the cure time being less than three hours. The beads were then washed twice with ten millimolar MOPS, with a final wash performed with deionized water for thirty minutes. Optimum parameters for a given protein-creatine suspension were logged and utilized without adjustment during further batch production.

The production of less than fifty milliliters of micro-beads was sufficient to meet the requirements of preliminary studies. Hence, the encapsulator resembled a batch-reactor. Commercial production of aqueous gel creatine particles has been optimized based on the aforementioned principle. As a result, this aqueous encapsulation methodology generates creatine monohydrate encapsulated in the presence of phosphate, glycerol and, black pepper, in a gelled hydrolyzed whey protein matrix.

Preparation of Oil-Core Encapsulation Systems:

A concentric system with two running liquids was essential for the generation of microcapsules with addition oil cores. This was achieved by simultaneously supplying two feed lines to a specifically designed concentric nozzle unit. This generated a co-extruded laminar liquid jet, which was subsequently broken-up into mononuclear drops by the application of a vibrational frequency. The creatine liquid ester carrier was then gelled into the desired mononuclear microcapsules, each comprising an inner oil core and a whey protein outer membrane.

The capsule diameter was mainly dependent on the diameter of the outer nozzle. As was the case for the single nozzle system used for aqueous systems, it was possible to vary the size within a certain range by increasing/decreasing the applied flow rate and vibrational frequency. The diameter of the internal nozzle and the flow rate of the material also affected the final capsule size. In particular, increasing diameters and volumes resulted in larger core volumes, therefore, larger microcapsules.

Micro-dispersed whey protein microcapsules were prepared based on laminar jet break-up for the generation of whey protein micro-capsules loaded with creatine monohydrate and bioperine. The liquid ester carrier was delivered to the nozzle via a feed line using two nozzles with diameters in the range twenty to a thousand micrometers. The nozzle was connected, via a PTFE membrane, to a vibrating device, which was insulated from the surrounding structures by rubber mounts to avoid the generation of resonance frequencies in the system.

Oil-based formulations were prepared. These comprised the bioactive material (e.g., creatine monohydrate), milk protein, a pharmacological agent (e.g., weak alcohol) and an organic acid (e.g., acetic acid). This combination of substrates naturally produced an acetate ester that was stable at room temperature. However, no salt was present to initiate protein polymerization. Therefore the suspension remained in a fluid state.

In a second formulation, creatine liquid ester was emulsified with black pepper extract, astaxanthin, and an oil-based agent such as alpha lipoic acid. This formulation would flow through the inner nozzle, which was heated to thirty-five degrees Celsius, and create the capsule's inner core. The outer capsule membrane was formed using the creatine liquid ester in the presence of additional phosphate, which was supplied to the outer nozzle using an air-pressure regulator that enabled flow rates ranging from five to ten liters per hour at an air pressure no greater than 0.7-0.9 bar.

At this point, the pH rose and the ester reacted with the base to release an acetate salt that instantly polymerized the protein suspension with simultaneous encapsulation of bioperine, glycerol, phosphate, astaxanthin, and alpha lipoic acid within the core with bioactive material, e.g., creatine. This reaction produced residual amounts of alcohol, which was subsequently removed during the final drying process, to avoid the presence of alcohol in food.

Having chosen flow rates that enabled a stable jet of creatine droplets through the nozzles, frequency and electrostatic charge were then set to promote a stable bead chain that would be visible in the strobe light and to cause circular dispersion of the drops as they fell into a gelling bath that was placed fifteen centimeters under the nozzle.

The production of less than fifty milliliters of micro-beads was sufficient to meet the requirements of preliminary studies. Hence the encapsulator resembled a batch-reactor.

The protein-creatine-ester blend was aseptically extruded through the assigned nozzle into 0.4M alkaline phosphate buffer tempered to thirty-five degrees Celsius. The buffer was continuously agitated agitation to avoid coalescence or flocculation of microcapsules during the curing process. The gelling bath comprised five hundred milliliters of di-sodium phosphate buffer in 10 mM MOPS with 0.04-0.07% w/v glycerol. The gelling bath was maintained at a pH of 7.4 and also stirred magnetically to form a visible vortex. Droplet immersion of creatine into this curing solution caused the instantaneous release of the acetate salt that polymerized the hydrolyzed protein. This further encapsulated the creatine moiety within the capsule core and outer whey protein membrane.

Some practices feature inducing a charge to the mononuclear droplets to promote their dispersion and also to prevent coalescence from occurring either in the air and/or upon impact, which could result in the formation of duplets and/or larger microcapsules. This charge must be applied at higher values compared to the mono-centric nozzle system to enable similar droplet dispersion to be achieved. This is due to the smaller percentage of polyelectrolyte present in the droplet because of the core material.

Upon landing in the phosphate gelling bath, high surface-tension momentarily retards droplet movement. This can lead to formation of oval capsules. In some instances this delay can cause the droplet to burst, thus releasing the creatine liquid ester carrier before encapsulation takes place. It is hypothesized that this bursting is caused by the movement of the core liquid out through the pre-hardened membrane protein when capsules are been held back briefly at the surface of the hardening solution and hence results in release, by bursting, of the core creatine liquid.

To avoid the deleterious effects of high surface tensions, it is useful to reduce the surface tension by either adding a surfactant or by slightly heating the phosphate solution, for example to a temperature that is between fifteen and sixty degrees Celsius. This promotes quicker entry of the drop into the solution and thereby suppresses its tendency to deform otherwise. It also results in immediate encapsulation and thus results in a more efficient encapsulation procedure.

For this reason, it is particularly useful to include glycerol in the phosphate gelling bath and to temper the bath to about thirty-five degrees Celsius. As a side benefit, having glycerol in the bath results in incorporation of the glycerol into the final creatine capsule. This permits the consumer to enjoy the functional and ergogenic benefits of of glycerol's favorable hydration properties for muscle function.

During jet break-up and/or when entering the gelling bath, a high negative charge was induced onto their surface by exposing the drop to an electrical potential of up to 2.15 kilovolts between the nozzle and an electrode that is placed directly underneath the nozzle. As creatine droplets fall through the resulting electric field, they are deflected from their vertical path. This results in the drops' impact on the gelling bath occurring over a larger area. This enabled mono-dispersed microcapsules with a standard size deviation of less than ±1.5% to be generated.

Within the gelling bath, several essentially instantaneous reactions occur. When a droplet enters the gelling bath, the pH increases and the ester reacts with the base to release an acetate salt that instantly polymerizes the protein suspension with simultaneous encapsulation of bioperine, glycerol, phosphate and bioactive material, e.g., creatine. This reaction produces residual amounts of alcohol, which is subsequently removed during the final drying process, thereby avoiding the contamination of food with alcohol.

Pliable micro-beads were cured and/or polymerized at room temperature in the phosphate buffer, recovered, and washed twice in sterile water. A matrix characterization was then performed as a function of cure time in the buffer, with the cure time varying between zero and three hours. The product was then washed twice with 10 mM MOPS, with a final wash performed with deionized water for thirty minutes. Optimum parameters for a given protein-creatine suspension were logged and used without adjustment during further batch production.

The production of fewer than fifty milliliters of microbeads was sufficient to meet the requirements of preliminary studies. Hence the encapsulator resembled a batch-reactor. Commercial production of aqueous gel creatine particles has been optimized based on the aforementioned principle. As a result, this aqueous encapsulation methodology generates creatine monohydrate encapsulated in the presence of phosphate, glycerol and, black pepper, in a gelled hydrolyzed whey protein matrix. This oil-based encapsulation system generates creatine monohydrate encapsulated within an alpha-lipoic acid oil core in the presence of phosphate, glycerol, and black pepper, further surrounded by an outer membrane of hydrolyzed whey protein.

The incorporation of bioperine to the formulation enhances the absorption efficiency of the bioactive within the gastro-intestinal tract. The presence of hydrolyzed milk protein eliminates the allergenic nature of the final product. This formulation has been optimized for the production of more than a thousand kilograms of encapsulated bioactive in a single batch under sterile conditions.

The proposed aqueous and oil-core microcapsules containing encapsulated creatine can be manufactured using the aforementioned techniques on large-sale, for example more than four hundred liters per day, by using vibrating jet technology and subsequently drying by either drum drying or fluidized-bed drying. The dried product can then be stored for subsequent addition to a beverage to assist creatine bioavailability in the blood and, more importantly bio accessibility of the creating to the muscle during exercise.

X-ray diffraction (XRD) is a versatile, non-destructive technique utilized to detail the chemical composition and crystallographic structure of creatine monohydrate before and after the encapsulation process. In order to better convey an understanding of the fundamental principles of X-ray diffraction instruments, the terms "amorphous" and "crystalline" are defined below.

In the "amorphous" state, atoms are randomly arranged as they would be in a liquid. Whey protein is amorphous.

In a "crystalline" state, there exists a lattice, which is regular three-dimensional distribution of atoms in space. A variety of lattices exist, among which are cubic and rhombic lattices. These atoms are arranged so that they form a series of parallel planes separated from one another by a distance, d, that varies according to the nature of the material. For any crystal, planes exist in a number of different orientations, each with its own specific d-spacing.

Commercial creatine monohydrate, in its raw form, is in a first crystalline form that reacts readily with water. This form is somewhat unstable. It is therefore desirable to transform it into a second crystalline form, which is more stable.

Figure 3:
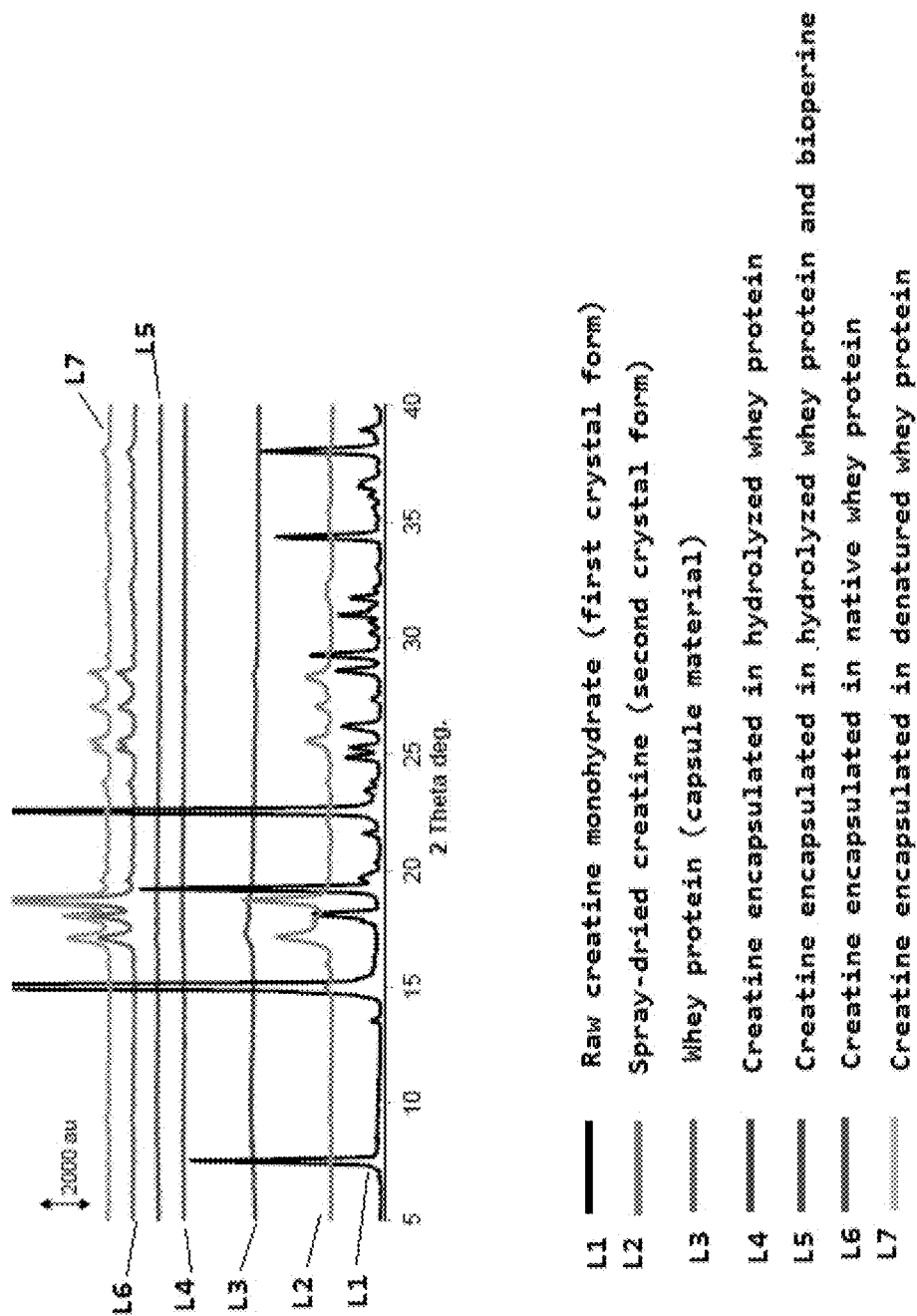
FIG. 3 shows X-ray diffraction data for consecutive steps within an encapsulation process.

FIG. 3 shows X-ray diffraction data representative of creatine stability. After molecular stabilization, creatine monohydrate appears to be less amorphous. This makes it less vulnerable to creatinine production.

X-ray diffraction analysis also serves as a successful method to determine encapsulation efficiency of the system. This is because creatine is crystalline and whey protein, which serves as the encapsulation matrix, is amorphous. Hence, if creatine is successfully encapsulated by whey protein, X-ray diffraction will not show any crystalline structures. This is because all the creatine would have been amorphous whey protein.

However, if creatine is only partially encapsulated by whey protein, X-ray diffraction data would reveal the existence of some crystalline material. This would suggest the existence of free crystalline creatine that has not interacted with whey protein.

In FIG. 3, X-ray diffraction data illustrates commercial (raw) creatine monohydrate on the baseline curve L1 to be clearly crystalline. The intensity of the two peaks midway along the profile reveals this first crystalline form.

Following molecular stabilization using low-temperature spray-drying, the second crystalline form is generated. The existence of this second crystalline form is manifested in lesser intensity of crystalline peaks illustrated for the L2 curve. Whey protein encapsulation material was also analyzed to confirm this amorphous form of whey protein and this was validated in the L3 curve.

During the encapsulation process, specialized hydrolyzed whey protein demonstrated successful encapsulation efficiency for creatine monohydrate. Interestingly addition of bioperine did not adversely affect the encapsulation efficiency and full encapsulation capacity in the X-ray diffraction profile, as shown in curve L5. However utility of native and denatured whey protein failed to successfully encapsulate creatine.

Based on the results shown in FIG. 3, it is evident that creatine is efficiently encapsulated using hydrolyzed whey protein in the presence of bioperine for enhanced absorption capacity. It is clear that the first step generated an appropriate molecular structure for efficient creatine encapsulation with hydrolyzed whey protein in the presence of bioperine.

Figure 4:
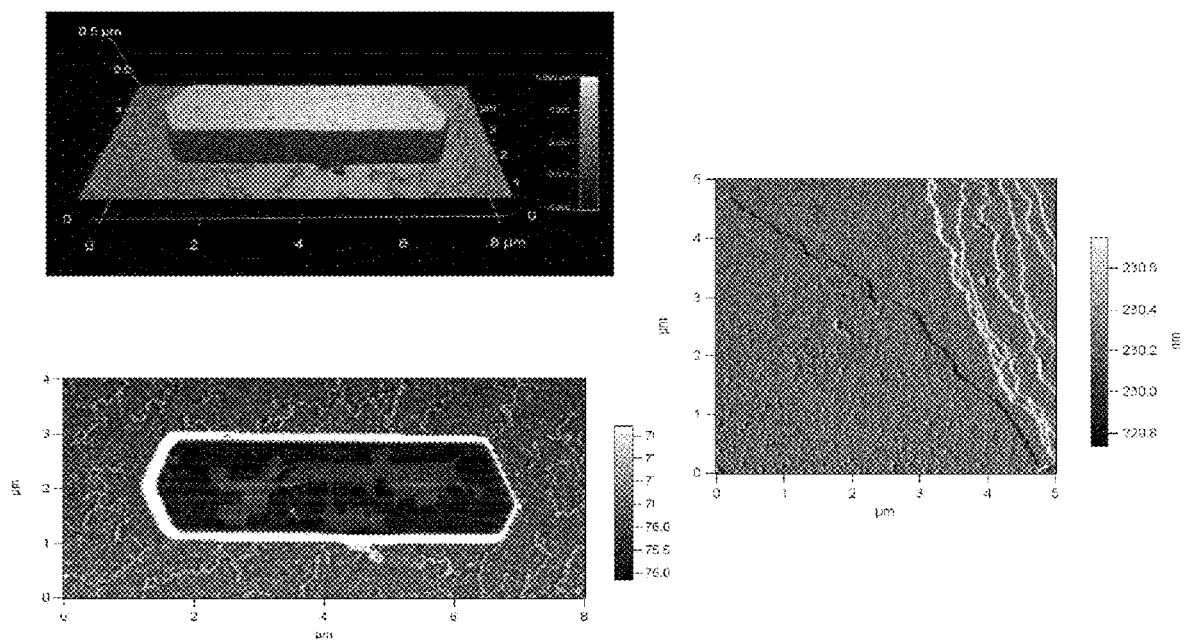
FIG. 4 shows data from an atomic force microscope illustrating the presence of a second form of the creatine crystal within milk protein encapsulation matrices.

FIG. 4 shows atomic force microscopy data illustrating the existence of embedded creatine monohydrate crystals within milk protein encapsulation systems. These crystals have taken the second crystal form, thus promoting protection of creatine from water. Individual creatine crystals having an approximate size of between ten and twenty micrometers may solely occupy a whey protein capsule. However the functionality remains the same per batch of encapsulated creatine produced.

Thermal Stability

Figure 5:
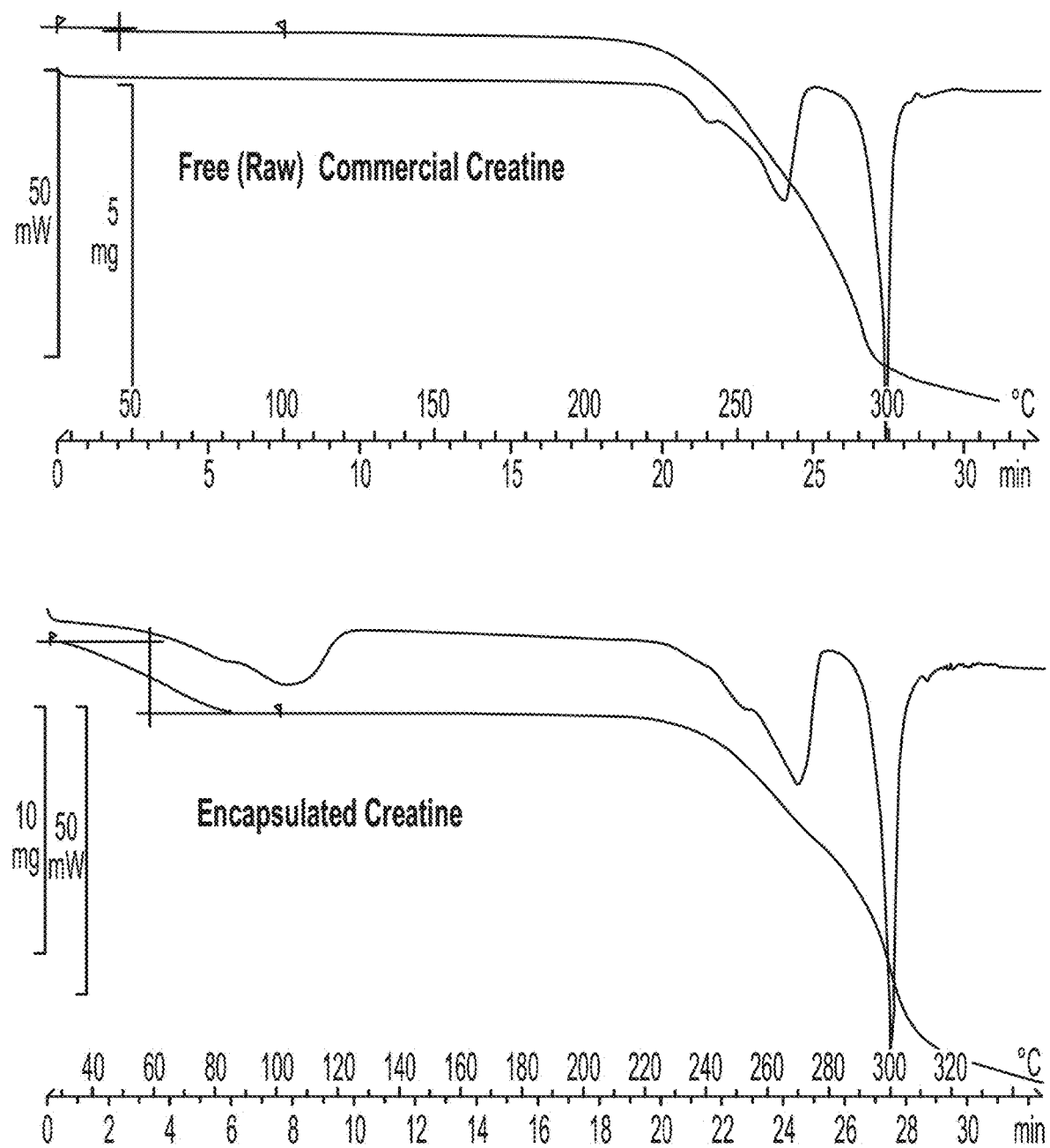
FIG. 5 shows thermal gravimetrical analysis data of free creatine and encapsulated creatine.

The thermal gravimetrical analysis data shown in FIG. 5 compares raw and encapsulated creatine. Based on this data, there was no change in the thermal properties or compositional structure of commercial creatine as a result of having been encapsulated. The thermal gravimetrical analysis thus demonstrates that the degradation temperature of creatine remained the same before and after encapsulation. Hence, in the presence of encapsulation structures, creatine does not undergo undesirable degradation. Furthermore, weight fluctuations were unaffected by changes in temperature. This illustrates that the creatine monohydrate retained its compositional structure and reactive properties following encapsulation.

Figure 6:
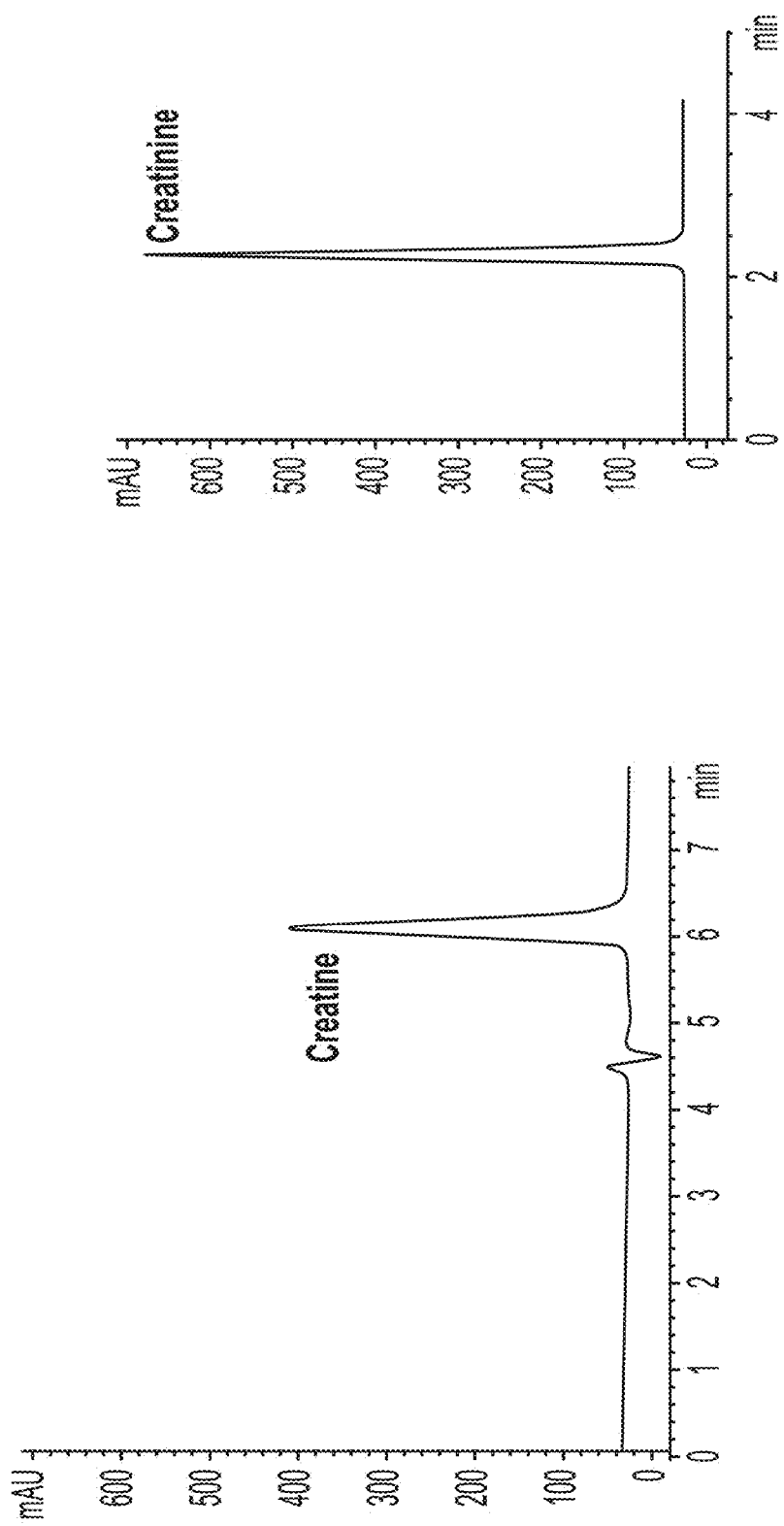
FIG. 6 shows creatine and creatine detection by high-performance liquid chromatography ("HPLC") whereby creatine eluted after 2.25 minutes and creatine generated a narrow peak after 6.1 minutes.

FIG. 6 shows detection of creatine and creatinine concentrations using standardized high-performance liquid chromatography. Following validation of the high-performance liquid chromatography technique, stability trials were performed for free and encapsulated creatine in water held at twenty-five degrees Celsius for ten hours.

The results demonstrated that degradation of free creatine followed first-order kinetics. Based on the slope of the line, the first-order degradation rate constant was calculated as 0.0263 per day at twenty-five degrees Celsius for free creatine monohydrate.

Substantial conversion of creatine into creatinine was recognized in aqueous formulations. These demonstrated significant differences from those identified for encapsulated creatine.

Encapsulated formats revealed that no creatine had been converted into creatinine in the presence of water after twelve hours. Even after forty-eight hours of continued storage, there was no evidence of creatinine production. This validates the encapsulation conditions used for the protection of creatine in beverages, particularly beverages that are intended as supplements used by athletes engaging in sports.

Figure 7A:
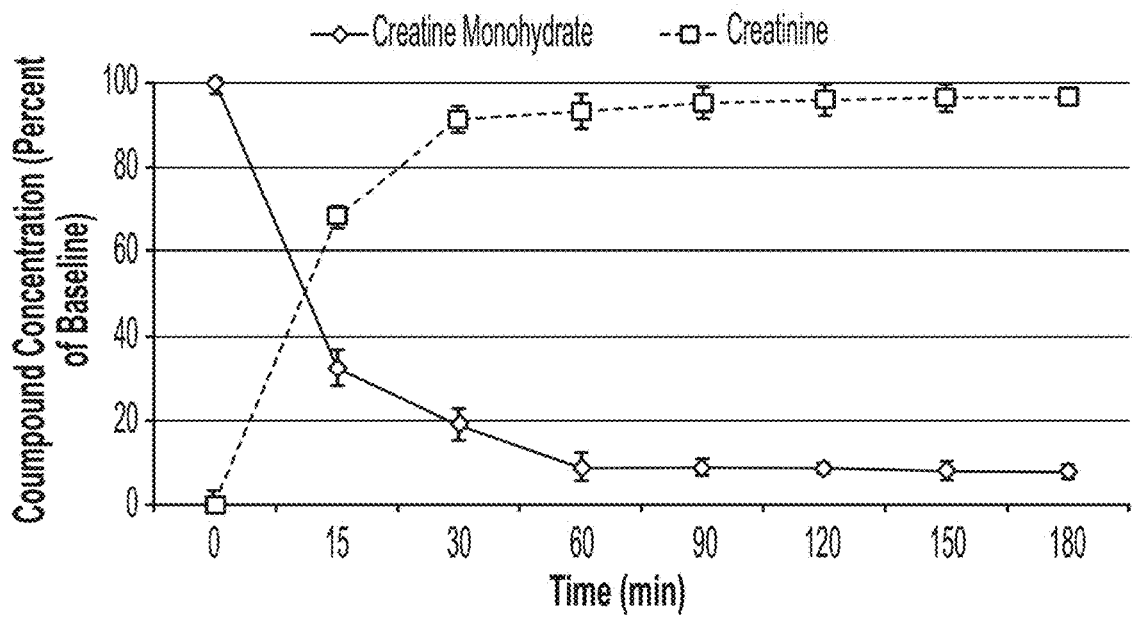
FIGS. 7A and 7B show commercial creatine monohydrate degradation in the aqueous incubation medium compared to encapsulated creatine with standard deviation being the average for eleven independent studies.
Figure 7B:
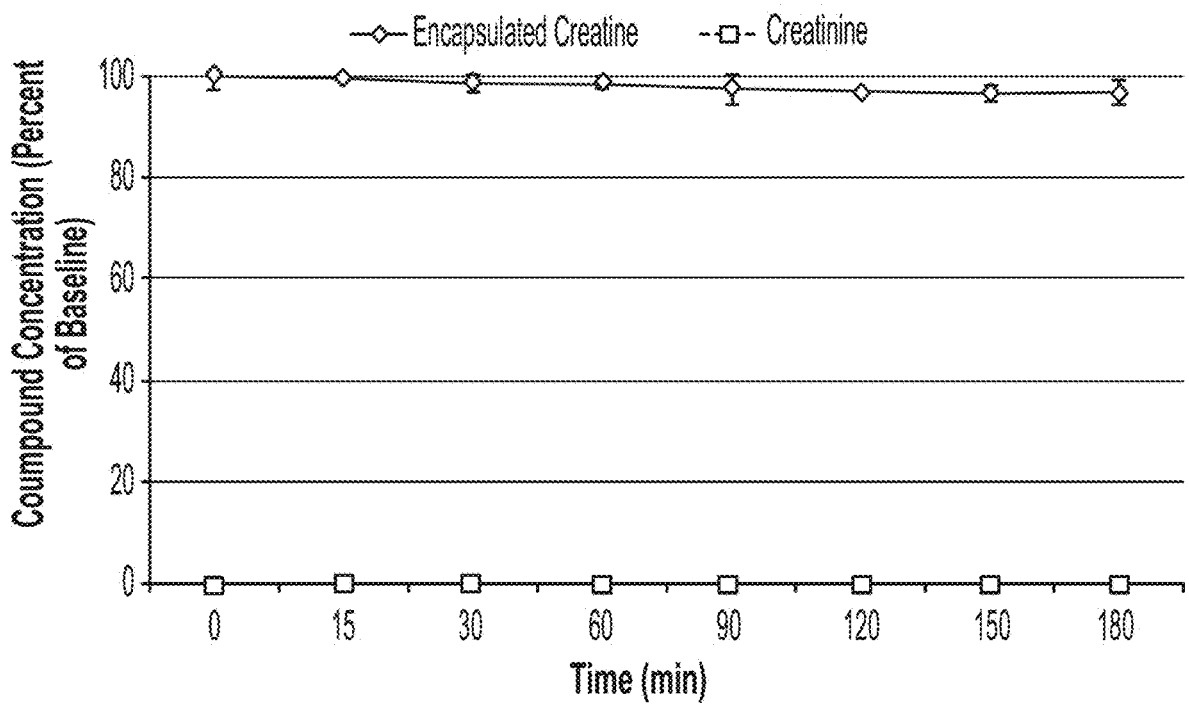

FIGS. 7A and 7B illustrate the creatine content reduction in water.

FIG. 7A shows that the concentration of commercial creatine monohydrate fell by 66% following only fifteen minutes of incubation in water at room temperature. After an hour, only about 9%±1.34% of the initial creatine concentration remained. This reduction demonstrates a direct correlation with an increase in creatinine formation after fifteen minutes.

In contrast, as shown in FIG. 7B, encapsulated creatine was significantly more stable in water solution. Even after three hours at room temperature, there was no significant detection of creatinine. Hence, creatine encapsulation provides a useful delivery vehicle for creatine monohydrate in an aqueous beverage.

Following this, accelerated shelf-life tests were conducted with final sports-drink samples that were formulated according to industrial standards. Encapsulated creatine demonstrated more than three years of shelf-life stability in such aqueous environments. Furthermore, high-performance liquid chromatography analysis confirmed the absence of creatinine after completion of shelf-life testing. Hence, encapsulated creatine fulfilled the stability criteria for storage of beverage formulations.

The methods and compositions described herein provide milk-protein encapsulation vehicles with desired mechanical rigidity, resistance to deformation, strength, and resistance to fracture in order to structurally protect creatine monohydrate from aqueous solutions during long storage times with concomitant release at the required systemic target site. Microencapsulates as described herein demonstrated acceptable long-term storage stability, namely as much as three years, with further sustained stability in simulated stomach conditions in the presence of pepsin. Microscopy and chromatography further validated the targeted disintegration of protein matrices in physiological intestinal conditions after several minutes with bioperine providing enhanced absorption capacity.

The microbead degradation is catalyzed by the synergistic effect of a neutral pH and enzymatic action. This property is one that can be exploited for manufacture of specialized creatine sports supplements. For this reason, optimization of encapsulation conditions represented the basis of creatine stabilization in the presence of creatine protective chaperones, such as milk protein and bioperine.

Because bioperine is highly lipophilic, the concentration of bioperine potentially increases the lipophilicity of the creatine compound. This, in turn, would improve its ability to diffuse through biological membranes.

In contrast, creatine is lipophobic. As such, creatine generally requires a transporter to cross the lipid-rich plasma membrane of a typical cell. The methods disclosed herein result in a stable creatine-milk protein-bioperine moiety that demonstrated reduced creatine degradation and increased half-life in aqueous solutions. Hence, encapsulation in hydrolyzed milk protein represents an excellent matrix for site-specific controlled delivery and release of creatine with subsequent promotion of its absorption at their target site.

FIGS. 8A-8E shows images of the progression of creatine encapsulation in real-time.

Figure 8A:
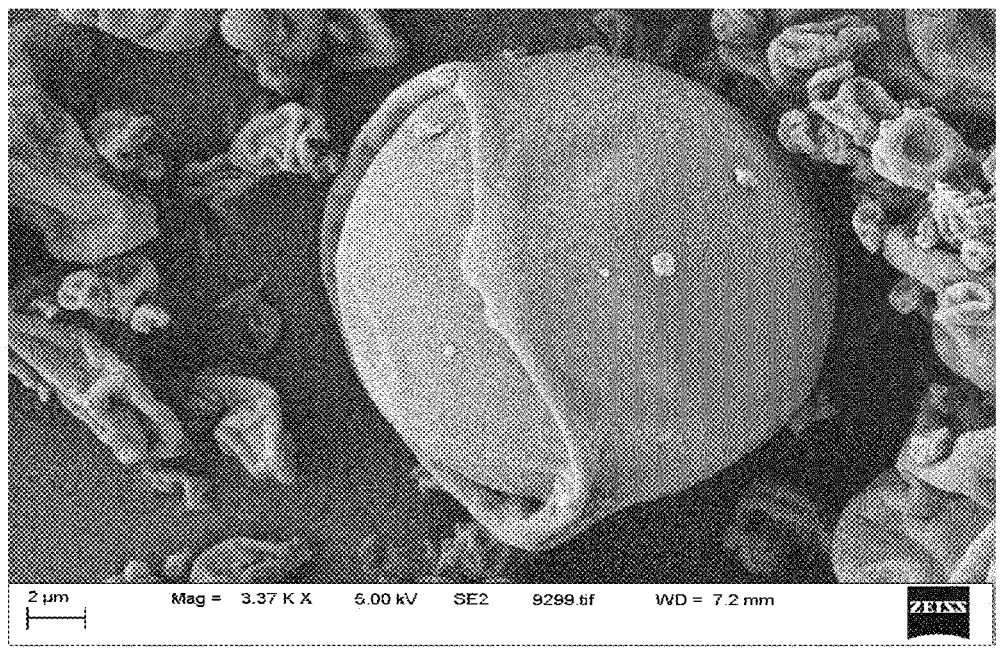
FIG. 8A is a scanning electron microscope image of an incomplete coating of creatine using native whey protein.
Figure 8B:
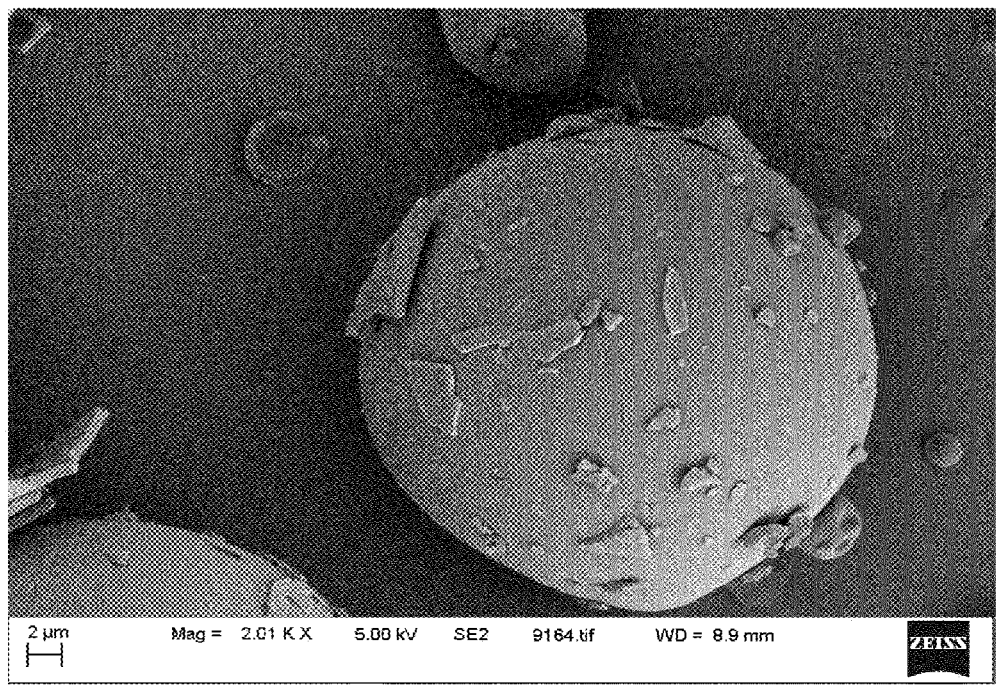
FIG. 8B is a scanning electron microscope image of a single encapsulated particle.

FIG. 8A shows partial encapsulation of creatine using native whey protein. It is apparent that encapsulation is not quite complete. This can be compared to FIG. 8B, in which the native whey protein has been replaced by hydrolyzed protein as an encapsulation matrix.

Figure 8C:
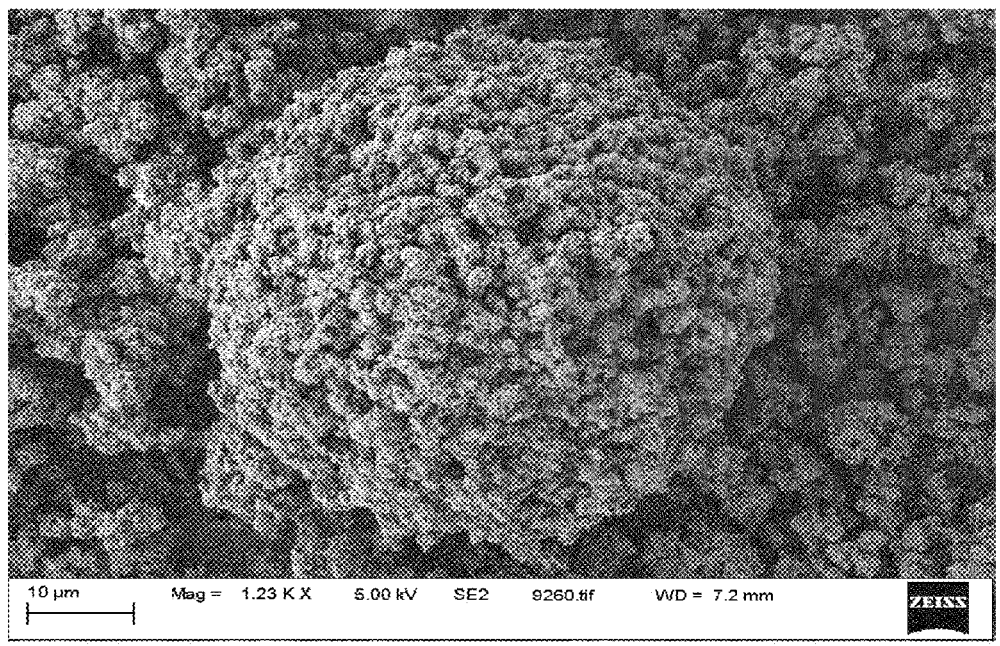
FIG. 8C is a scanning electron microscope image of an additional hydrolyzed protein coating

FIG. 8C shows creatine encapsulated in whey protein with bioperine outer membrane layers.

Figure 8D:
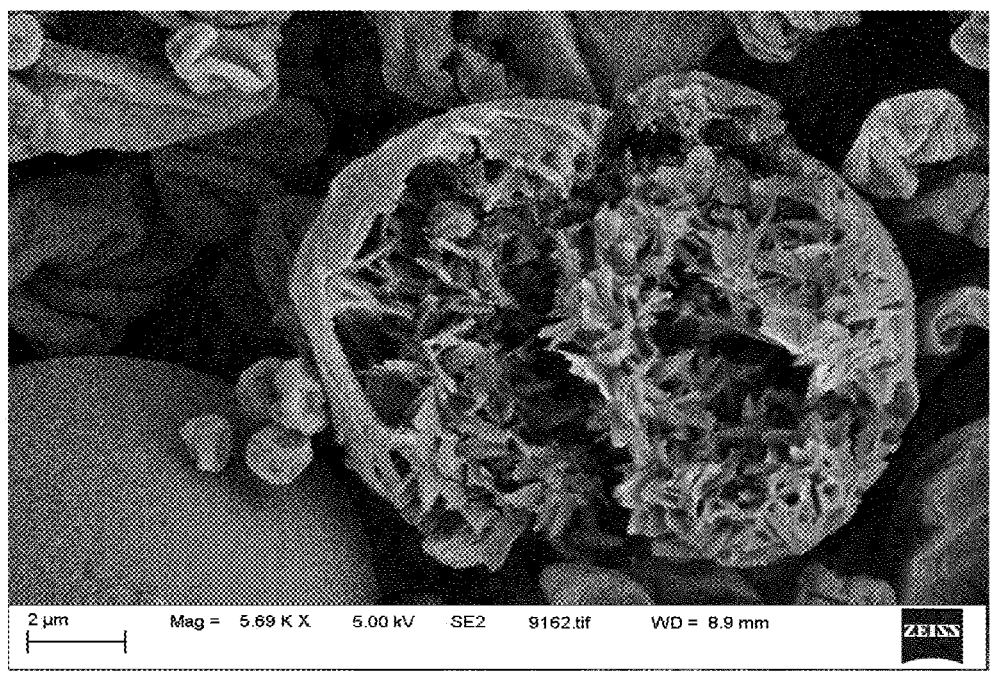
FIG. 8D is a scanning electron microscope image of a microparticle after initial intestinal digestion.
Figure 8E:
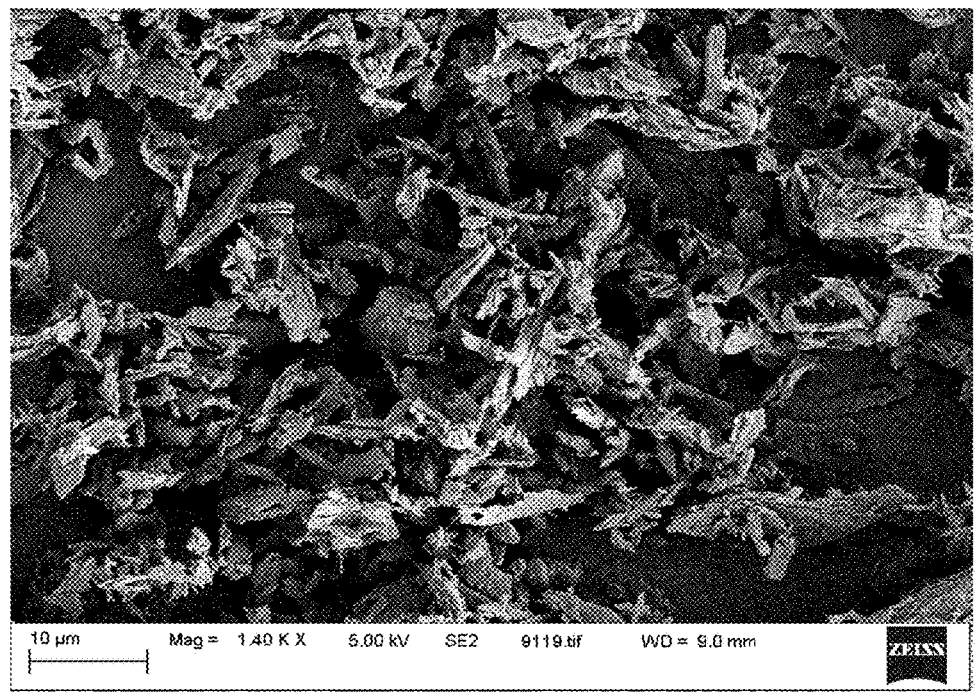
FIG. 8E is a scanning electron microscope image of released creatine for absorption into the bloodstream.

FIG. 8D shows the microcapsule having been partially digested as a result of intestinal incubation. In FIG. 8D, one can see erosion of protein matrix material as a result of the enzymatic action of intestinal contents. After about three minutes of intestinal incubation, creatine monohydrate was fully released for subsequent absorption.

Creatine Storage Stability and Ex Vivo Digestion

The ability to adhere to the intestinal epithelium is important for rapid absorption of encapsulated material into the blood stream. As such, an important factor for efficacious encapsulation of creatine is the extent to which the microparticles adhere to the intestinal epithelium after intestinal liberation of the encapsulated creatine.

Whey protein micro-particles have been found to be suitable ex vivo delivery vehicles for delivery of active creatine along a porcine gastro-intestinal tract with ileal tissue adhesion indicating rapid absorption into the blood stream. After twenty-eight days of storage in an aqueous solution at a pH of four, creatine encapsulated in hydrolyzed protein illustrated almost no loss in creatine concentration. Furthermore, creatinine was not detected at any significant levels after 28-day storage in hydrolyzed milk protein encapsulation systems.

Figure 9:
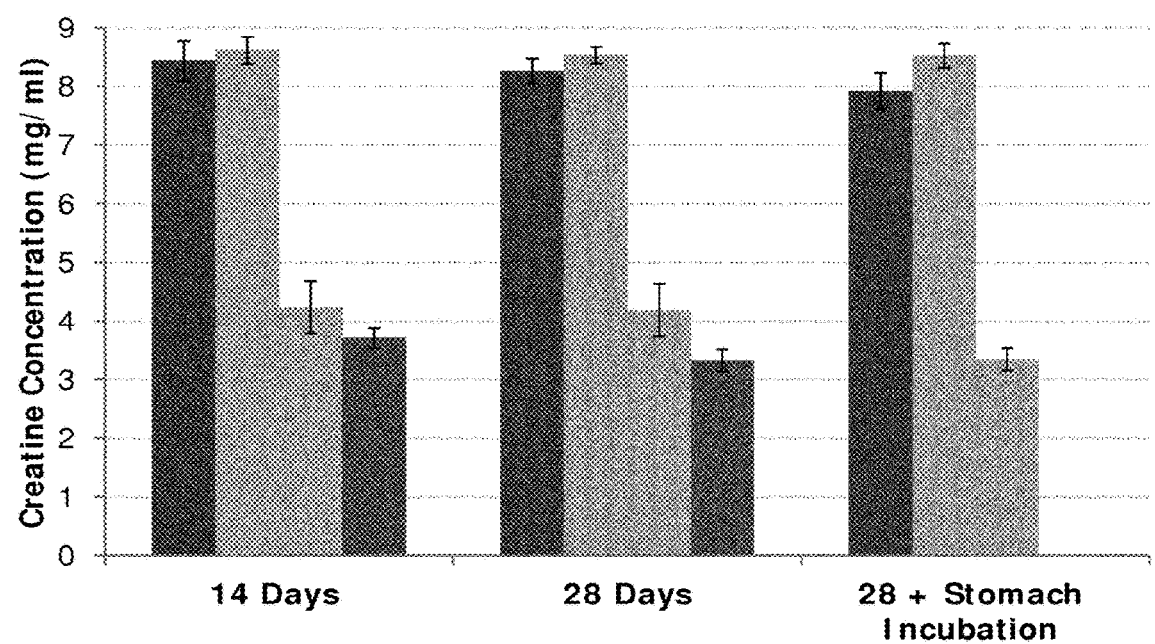
FIG. 9 shows concentration of creatine monohydrate during 28-day storage in aqueous solution at pH 4.0 at room temperature with four different treatments, namely hydrolyzed milk protein capsules, hydrolyzed milk protein capsules with bioperine, native whey protein capsules, and creatine in denatured whey protein capsules at 25° C. for up to 28 days followed by three hours of exposure to ex vivo stomach contents at a pH of 1.6 for three hours.
Figure 10:
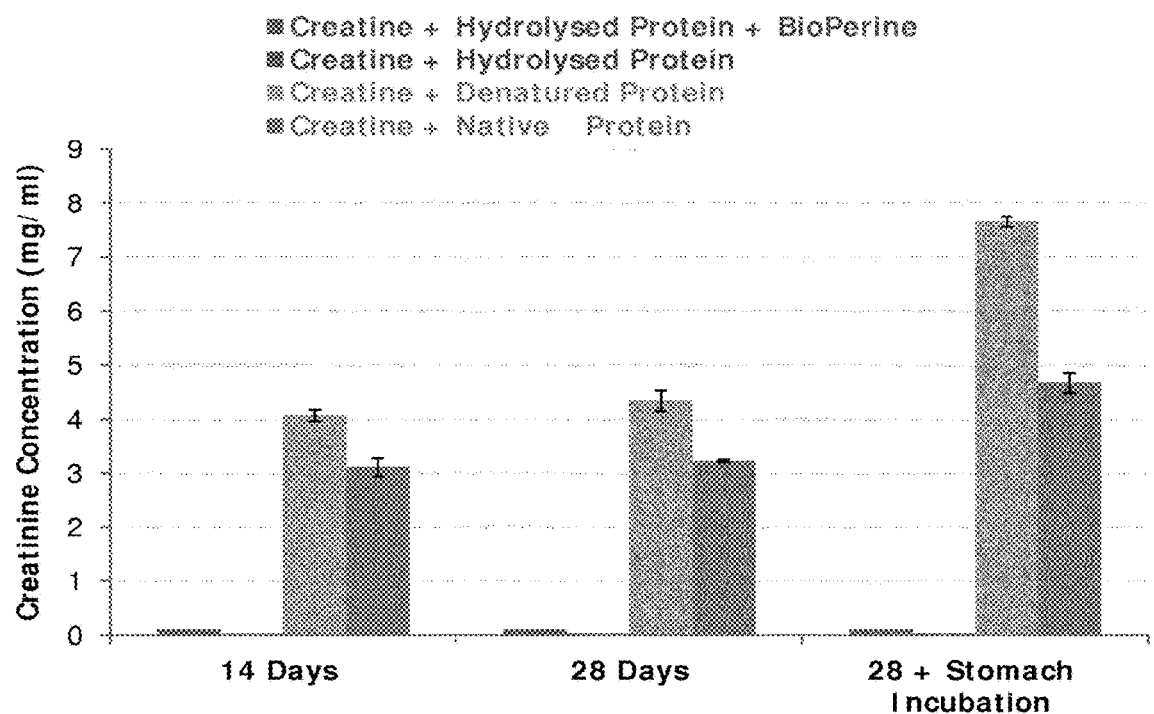
FIG. 10 shows concentration of creatinine during formation during 28-day storage in aqueous solution at pH 4.0 at room temperature with the following treatments: hydrolyzed milk protein capsules, hydrolyzed milk protein capsules with bioperine, native whey protein capsules, and creatine in denatured whey protein capsules at 25° C. for up to 28 days followed by three hours of exposure to ex vivo stomach contents at a pH of 1.6.

FIG. 9 shows that subsequent gastric incubation maintained complete creatine concentration with no detection of creatinine. Creatine encapsulated in various forms of milk protein failed to express significant protective properties for creatine after 28-day water storage as illustrated in FIG. 10. Therefore, native and denatured milk protein matrices expressed weak protective properties for creatine and resulted in significant increases in creatinine concentrations. Hence, hydrolyzed whey protein encapsulation systems represent the only treatment capable of providing storage stability and acid tolerance to creatine monohydrate during beverage storage and stomach incubation. Hydrolyzed protein provides an encapsulation vehicle capable of maintaining maximum creatine concentrations of about 8 milligrams per milliliter.

Absorption Capacity

Figure 11:
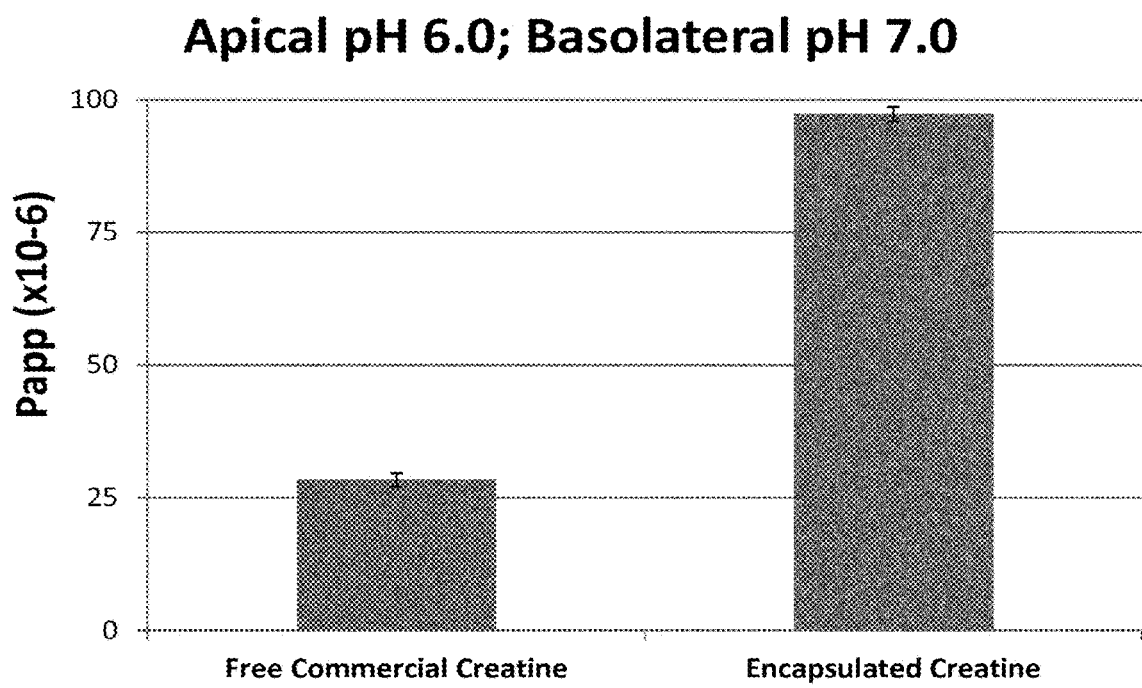
FIG. 11 shows various levels of creatine absorption tested using standard absorption tests involving Caco-2 monolayers, including tests of apical to basolateral permeability of free and encapsulated creatine to mimic in vivo conditions, with the apical permeability at a pH of six and the basolateral permeability at a pH of seven.

Various levels of creatine absorption were tested using standard absorption tests involving Caco-2 monolayers. Apical to basolateral permeability of free and encapsulated creatine were tested and prepared to mimic in vivo conditions i.e., apical pH=6.0/basolateral pH=7.0). FIG. 11 shows that creatine absorption was significantly enhanced as a result of electrostatic interaction with bioperine. Electrophoretic mobility data demonstrated that free creatine had a zeta potential of −2.4 mV compared to −23.14 mV for creatine in the presence of bioperine. Hence, creatine absorption was significantly enhanced as a result of the electrostatic interaction generated during the formation of the creatine-bioperine complex during the encapsulation process.

As illustrated in FIG. 11, it is clear that absorption of encapsulated creatine was highly dependent on molecular charge of creatine i.e., encapsulated creatine generated the substantial molecular charge in the presence of bioperine at the pH utilized during encapsulation. Hence electrostatic potential of encapsulated creatine provided sufficient aqueous solubility for creatine solubility in fluids of the absorption site and lipid solubility in the presence of bioperine to allow sufficient partitioning of creatine into lipoidal membranes and systemic circulation.

The invention is not limited to the embodiments herein before described which may be varied in construction and detail without departing from the spirit of the invention.

The invention claimed is:

1. A manufacture comprising a microcapsule, wherein said microcapsule comprises an active component encapsulated within a polymerized hydrolyzed protein shell.

2. The manufacture of claim 1, wherein said microcapsule is of average diameter as determined by a laser diffractometer, wherein said average diameter is 20 to 1000 micrometers.

3. The manufacture of claim 1, wherein said microcapsule is of average diameter as determined by a laser diffractometer, wherein said average diameter is less than one hundred micrometers.

4. The manufacture of claim 1, wherein the active component is selected from the group consisting of a creatine moiety, L-glutamine, L-leucine, beta-alanine, and a branched chain amino acid.

5. The manufacture of claim 1, wherein the active component is a creatine moiety.

6. The manufacture of claim 1, wherein the active component is selected from the group consisting of a creatine salt, a creatine complex, and a creatine derivative.

7. The manufacture of claim 1, wherein the hydrolyzed protein comprises hydrolyzed whey protein.

8. The manufacture of claim 1, wherein the microcapsule further comprises pepper extract.

9. The manufacture of claim 7, wherein the pepper extract is bioperine.

10. The manufacture of claim 1, wherein the microcapsule further comprises astaxanthin dissolved in a fatty acid.

11. The manufacture of claim 1, wherein the microcapsule further comprises a phosphate crosslinker that crosslinks amino acids in the polymerized hydrolyzed protein chains.

12. The manufacture of claim 1, wherein the microcapsule further comprises a phosphate crosslinker, that crosslinks amino acids in the polymerized hydrolyzed protein chains, wherein the polymerized hydrolyzed protein comprises glycerol.

13. The manufacture of claim 1, wherein the microcapsule further comprises 10-25% hydrolyzed protein (w/v).

14. The manufacture of claim 1, wherein the microcapsule comprises 75-90% active component (w/v).

15. The manufacture of claim 1, wherein the microcapsule comprises 1.0-0.5% pepper extract (w/v).

16. The manufacture of claim 1, wherein the microcapsule comprises 10-20% hydrolyzed protein (w/v), 80-90% active component (w/v), and 0.01-0.05% pepper extract (w/v).

17. The manufacture of claim 16, wherein the microcapsule further comprises a phosphate moiety.

18. The manufacture of claim 1, wherein said microcapsule comprises 10-20% hydrolyzed protein (w/v), 80-90% active component (w/v), and 0.01-0.05% bioperine (w/v).

19. The manufacture of claim 18, wherein the microcapsule further comprises a substance selected from the group consisting of a phosphate moiety, 0.04-0.07% glycerol (w/v), 0.03-0.08% astaxanthin (w/v), and 0.6-0.9% alpha-lipoic acid (w/v).

20. The manufacture of claim 1, wherein the microcapsule comprises 10-20% hydrolyzed protein (w/v), 80-90% active component (w/v), 0.01-0.05% bioperine (w/v), a phosphate moiety, 0.04-0.07% glycerol (w/v), 0.03-0.08% astaxanthin (w/v), and 0.6-0.9% alpha-lipoic acid (w/v).

21. The manufacture of claim 1, wherein the microcapsule is stable in water for a period of at least twenty-eight days.

22. The manufacture of claim 1, further comprising a multiplicity of additional microcapsules, wherein each of said additional microcapsules comprises an active component encapsulated within a polymerized hydrolyzed protein shell, said microcapsule having an average diameter of less than 100 micrometers as determined by a laser diffractometer.

23. The manufacture of claim 21, wherein said manufacture is selected from the group consisting of a comestible sports nutrition product, a food, a beverage, a supplement, a powder, a particulate material, a unit dose product, and a tablet.

24. The manufacture of claim 1, wherein the enzymatically hydrolyzed protein has a degree of hydrolysis (% DH) of 18 to 85%.

* * * * *